US012735455B2

(12) United States Patent
Nash et al.

(10) Patent No.: US 12,735,455 B2
(45) Date of Patent: Sep. 15, 2026

(54) HEMOSTATIC ELASTIN-LIKE POLYPEPTIDES

(71) Applicant: UNIVERSITÄT BASEL, Basel (CH)

(72) Inventors: Michael Adam Nash, Basel (CH); Ivan Urosev, Zurich (CH)

(73) Assignee: UNIVERSITÄT BASEL, Basel (CH)

( * ) Notice: Subject to any disclaimer, the term of this patent is extended or adjusted under 35 U.S.C. 154(b) by 741 days.

(21) Appl. No.: 18/042,001

(22) PCT Filed: Aug. 17, 2021

(86) PCT No.: PCT/EP2021/072863
§ 371 (c)(1),
(2) Date: Feb. 17, 2023

(87) PCT Pub. No.: WO2022/038155
PCT Pub. Date: Feb. 24, 2022

(65) Prior Publication Data

US 2024/0010682 A1 Jan. 11, 2024

(30) Foreign Application Priority Data

Aug. 18, 2020 (EP) .................................... 20191629

(51) Int. Cl.
*C07K 7/08* (2006.01)
*A61K 38/10* (2006.01)
*A61P 7/04* (2006.01)

(52) U.S. Cl.
CPC ................ *C07K 7/08* (2013.01); *A61K 38/10* (2013.01); *A61P 7/04* (2018.01)

(58) Field of Classification Search
CPC .............. C07K 7/08; A61P 7/04; A61K 38/10
See application file for complete search history.

(56) References Cited

U.S. PATENT DOCUMENTS

| | | | | | |
|---|---|---|---|---|---|
| 5,250,516 | A * | 10/1993 | Urry | A61F 2/0063 | 514/21.8 |
| 5,854,387 | A * | 12/1998 | Urry | C07K 14/78 | 530/323 |
| 6,127,166 | A * | 10/2000 | Bayley | C07K 14/43504 | 435/325 |
| 8,846,624 | B2 * | 9/2014 | Chaikof | A61L 27/227 | 530/324 |
| 2013/0197359 | A1 * | 8/2013 | Park | A61N 2/002 | 600/431 |
| 2018/0111978 | A1 | 4/2018 | Annabi | | |

FOREIGN PATENT DOCUMENTS

| | | | | | |
|---|---|---|---|---|---|
| EP | 1422242 | A1 * | 5/2004 | A61L 31/16 |
| JP | 2001505539 | | 4/2001 | |
| JP | 2007197434 | * | 8/2007 | C07K 7/08 |
| JP | 2007197434 | A * | 8/2007 | C07K 7/08 |
| JP | 2014530066 | | 11/2014 | |
| WO | WO-2008033847 | A2 * | 3/2008 | A61L 15/32 |
| WO | 2011006069 | | 1/2011 | |
| WO | WO-2017103088 | A1 * | 6/2017 | A61P 43/00 |
| WO | WO-2017168183 | A1 * | 10/2017 | C30B 7/04 |

OTHER PUBLICATIONS

MacEwan et al., 2014, Applications of elastin-like polypeptides in drug delivery, J Control Release, 190: 314-330.*

Brindha J et al., "Revisiting the insights and applications of protein engineered hydrogels", Materials Science & Engineering C, vol. 95, Nov. 5, 2018 (Nov. 5, 2018), p. 312-327.

Hu Bi-Huang et al., "Rational Design of Transglutaminase Substrate Peptides for Rapid Enzymatic Formation of Hydrogels", J. Am. Chem. Soc., vol. 125, No. 47, Nov. 26, 2003 (Nov. 26, 2003), p. 14298-14299.

Matthew J. Glassman et al., "End Block Design Modulates the Assembly and Mechanics of Thermoresponsive, Dual-Associative Protein Hydrogels", Macromolecules, vol. 48, No. 6, Mar. 13, 2015 (Mar. 13, 2015), p. 1832-1842.

Alisa S. Wolberg, "Thrombin generation and fibrin clot structure", Elsevier Blood Reviews (2007) vol. 21, No. 3, Apr. 7, 2007 (Apr. 7, 2007), p. 131-142.

Yi-Nan Zhang et al., A Highly Elastic and Rapidly Crosslinkable Elastin-Like Polypeptide-Based Hydrogel for Biomedical Applications, Advanced Functional Materials 2015, 25, 4814-4826.

Sugimura et al., "Screening for the Preferred Substrate Sequence of Transglutaminase Using a Phage-displayed Peptide Library: Identification of Peptide Substrates for Tgase 2 And Factor XIIIA", The Journal of Biological Chemistry vol. 281, No. 26, pp. 17699-17706, Jun. 30, 2006.

* cited by examiner

*Primary Examiner* — Amber D Steele
(74) *Attorney, Agent, or Firm* — JMB Davis Ben-David

(57) ABSTRACT

The present invention relates to a hemostatic elastin-like polypeptide comprising a glutamine embedded in a Q-block sequence and, optionally, a lysine embedded in a K-block sequence. Under physiological setting, the Q-block sequence and the K-block sequence are recognized by human transglutaminase factor XIIIa and crosslinked with fibrin networks. The present invention also relates to the medical use of the polypeptide, to a nucleic acid sequence encoding the polypeptide, to an expression vector comprising the nucleic acid sequence, and to a cell comprising the nucleic acid sequence or the expression vector.

14 Claims, 13 Drawing Sheets

Specification includes a Sequence Listing.

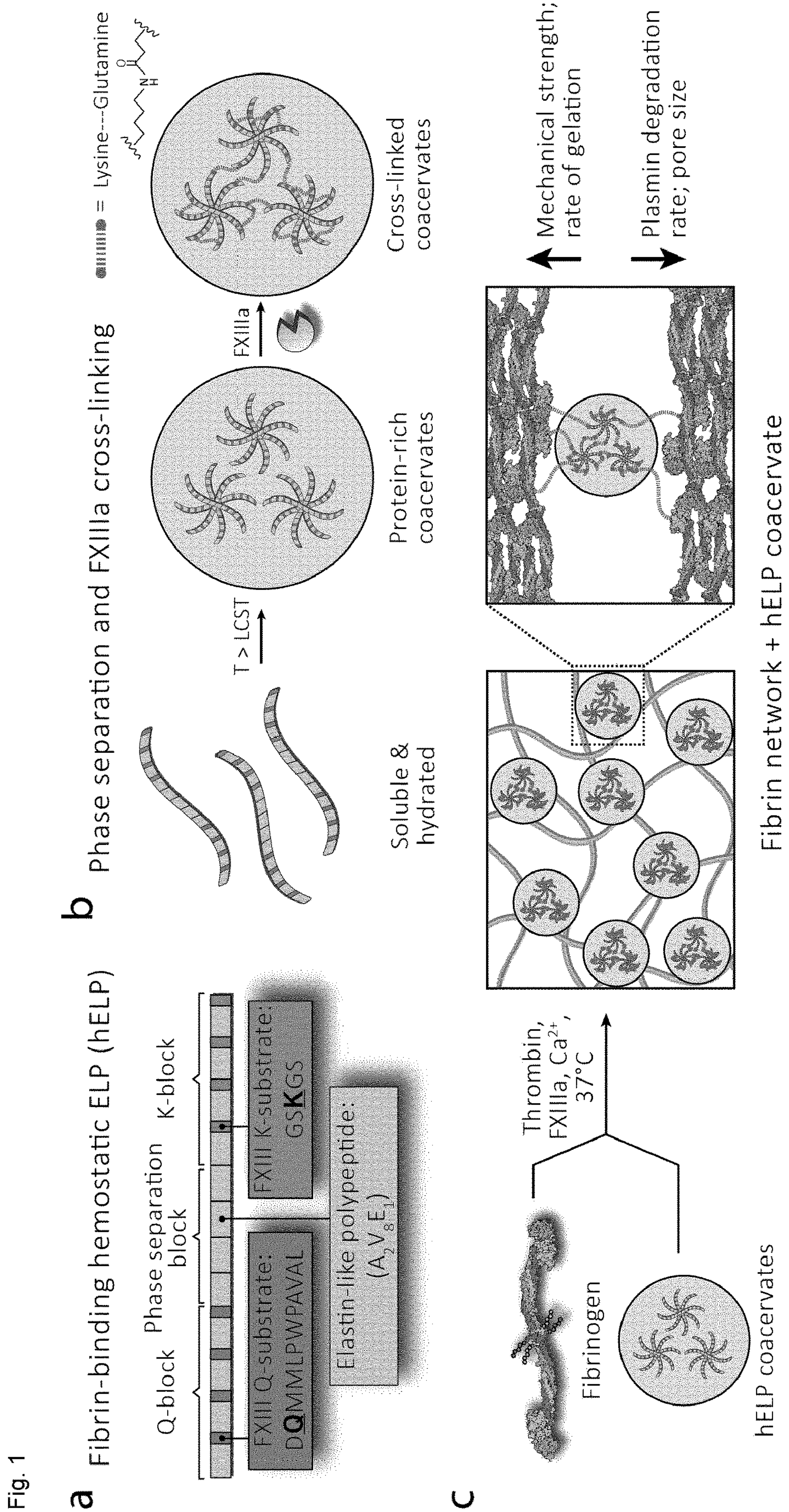
Fig. 1
a
Fibrin-binding hemostatic ELP (hELP)
Q-block
Phase separation block
K-block
FXIII Q-substrate: DQMMLPWPAVAL
FXIII K-substrate: GSKGS
Elastin-like polypeptide: (A2V8E1)
b
Phase separation and FXIIIa cross-linking
Soluble & hydrated
T > LCST
Protein-rich coacervates
FXIIIa
Cross-linked coacervates
= Lysine---Glutamine
c
Fibrinogen
hELP coacervates
Thrombin, FXIIIa, Ca2+, 37°C
Fibrin network + hELP coacervate
Mechanical strength; rate of gelation
Plasmin degradation rate; pore size Fig. 5
a
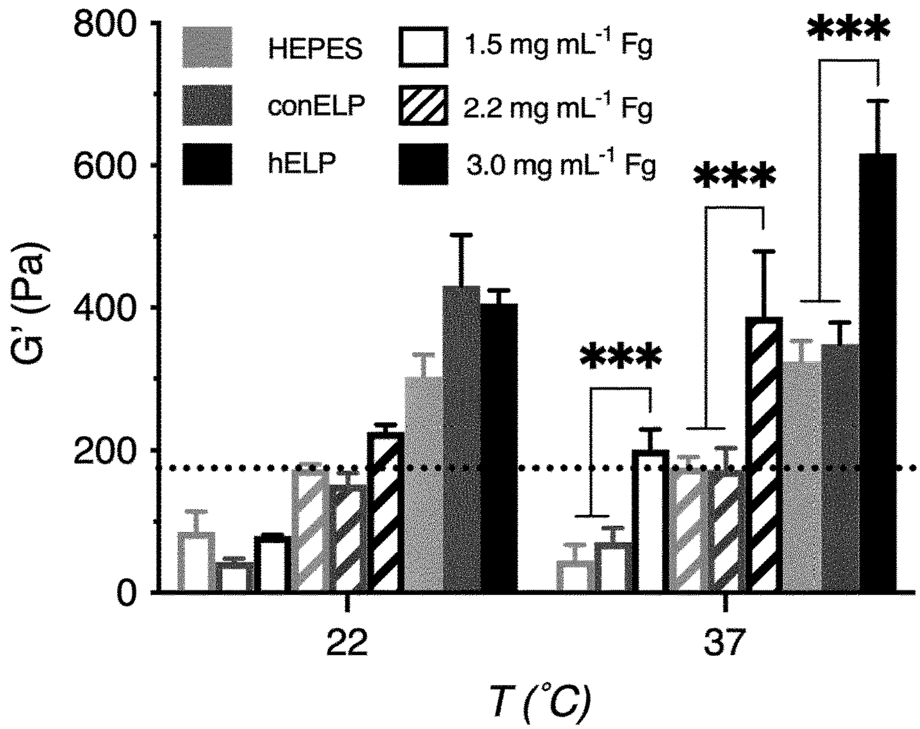
b
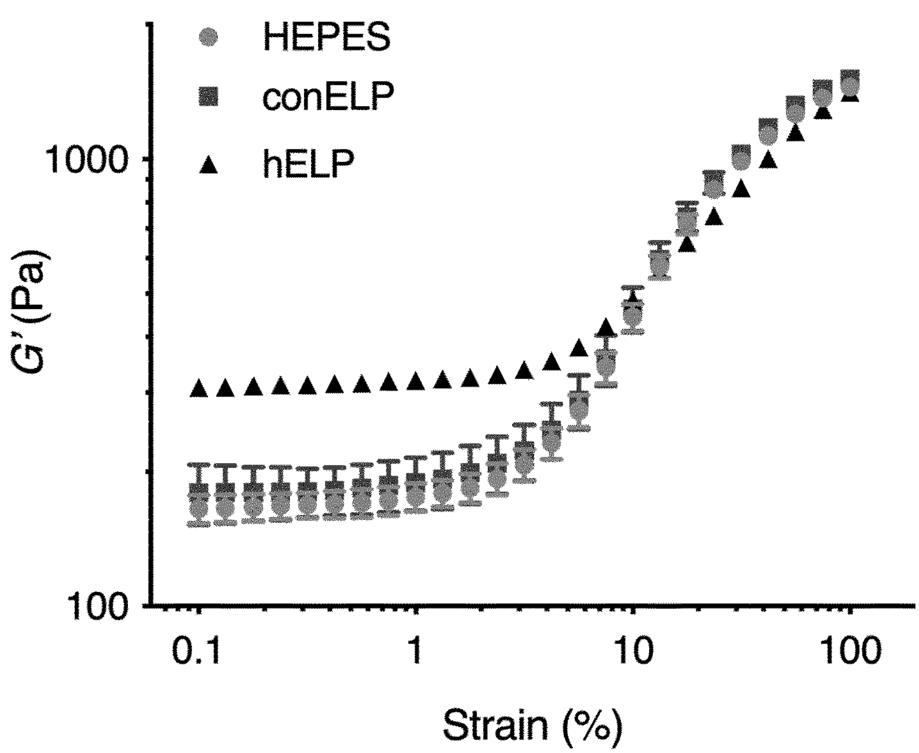

Fig. 12

SEQ ID NO: 1

Underlined: "spacer"/ELP repeats/VPGXG (SEQ ID NO: 12)

Bold: "Q block"/transglutaminase inhibitor (SEQ ID NO: 3)

*Bold and italics*: K-block sequences (SEQ ID NO: 11) deleted in SEQ ID NO: 16 and replaced with "Q block"/transglutaminase inhibitor (SEQ ID NO: 3)

MGHGVGVPGVGVPGAGVPGVGVPGVGVPGVGVPGVGVPGVGVPGVGVPGVGVPGEGVPGAGSGDQMMLPWP

AVALSGVPGVGVPGVGVPGAGVPGVGVPGVGVPGVGVPGVGVPGVGVPGVGVPGVGVPGEGVPGAGSGDQM

MLPWPAVALSGVPGVGVPGVGVPGAGVPGVGVPGVGVPGVGVPGVGVPGVGVPGVGVPGVGVPGEGVPGAG

SGDQMMLPWPAVALSGVPGVGVPGVGVPGAGVPGVGVPGVGVPGVGVPGVGVPGVGVPGVGVPGVGVPGEG

VPGAGSGDQMMLPWPAVALSGVPGVGVPGVGVPGAGVPGVGVPGVGVPGVGVPGVGVPGVGVPGVGVPGVG

VPGEGVPGAGVPGVGVPGVGVPGAGVPGVGVPGVGVPGVGVPGVGVPGVGVPGVGVPGVGVPGEGVPGAGV

PGVGVPGVGVPGAGVPGVGVPGVGVPGVGVPGVGVPGVGVPGVGVPGVGVPGEGVPGAGVPGVGVPGVGVP

GAGVPGVGVPGVGVPGVGVPGVGVPGVGVPGVGVPGVGVPGEGVPGAGVPGVGVPGVGVPGAGVPGVGVPG

VGVPGVGVPGVGVPGVGVPGVGVPGVGVPGEGVPGAGSG*GSKGS*SGVPGVGVPGVGVPGAGVPGVGVPGVG

VPGVGVPGVGVPGVGVPGVGVPGVGVPGEGVPGAGSG*GSKGS*SGVPGVGVPGVGVPGAGVPGVGVPGVGVP

GVGVPGVGVPGVGVPGVGVPGVGVPGEGVPGAGSG*GSKGS*SGVPGVGVPGVGVPGAGVPGVGVPGVGVPGV

GVPGVGVPGVGVPGVGVPGVGVPGEGVPGAGSG*GSKGS*SGVPGWLDSLEFIA

Fig. 13

SEQ ID NO: 016

Underlined: "spacer"/ELP repeats/VPGXG (SEQ ID NO: 12)

Bold: "Q block"/transglutaminase inhibitor (SEQ ID NO: 3)

MGHGVGVPGVGVPGAGVPGVGVPGVGVPGVGVPGVGVPGVGVPGVGVPGVGVPGEGVPGAGSGDQMMLPWP
AVALSGVPGVGVPGVGVPGAGVPGVGVPGVGVPGVGVPGVGVPGVGVPGVGVPGVGVPGEGVPGAGSGDQM
MLPWPAVALSGVPGVGVPGVGVPGAGVPGVGVPGVGVPGVGVPGVGVPGVGVPGVGVPGVGVPGEGVPGAG
SGDQMMLPWPAVALSGVPGVGVPGVGVPGAGVPGVGVPGVGVPGVGVPGVGVPGVGVPGVGVPGVGVPGEG
VPGAGSGDQMMLPWPAVALSGVPGVGVPGVGVPGAGVPGVGVPGVGVPGVGVPGVGVPGVGVPGVGVPGVG
VPGEGVPGAGVPGVGVPGVGVPGAGVPGVGVPGVGVPGVGVPGVGVPGVGVPGVGVPGVGVPGEGVPGAGV
PGVGVPGVGVPGAGVPGVGVPGVGVPGVGVPGVGVPGVGVPGVGVPGVGVPGEGVPGAGVPGVGVPGVGVP
GAGVPGVGVPGVGVPGVGVPGVGVPGVGVPGVGVPGVGVPGEGVPGAGVPGVGVPGVGVPGAGVPGVGVPG
VGVPGVGVPGVGVPGVGVPGVGVPGVGVPGEGVPGAGSGDQMMLPWPAVALSGVPGVGVPGVGVPGAGVPG
VGVPGVGVPGVGVPGVGVPGVGVPGVGVPGVGVPGEGVPGAGSGDQMMLPWPAVALSGVPGVGVPGVGVPG
AGVPGVGVPGVGVPGVGVPGVGVPGVGVPGVGVPGVGVPGEGVPGAGSGDQMMLPWPAVALSGVPGVGVPG
VGVPGAGVPGVGVPGVGVPGVGVPGVGVPGVGVPGVGVPGVGVPGEGVPGAGSGDQMMLPWPAVALSGVPG
WLDSLEFIA

SEQUENCE LISTING

```
<160> NUMBER OF SEQ ID NOS: 16

<210> SEQ ID NO 1
<211> LENGTH: 833
<212> TYPE: PRT
<213> ORGANISM: Artificial Sequence
<220> FEATURE:
<223> OTHER INFORMATION: Full hELP

<400> SEQUENCE: 1

Met Gly His Gly Val Gly Val Pro Gly Val Gly Val Pro Gly Ala Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Glu Gly Val Pro Gly Ala Gly Ser Gly Asp
    50                  55                  60

Gln Met Met Leu Pro Trp Pro Ala Val Ala Leu Ser Gly Val Pro Gly
65                  70                  75                  80

Val Gly Val Pro Gly Val Gly Val Pro Gly Ala Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
```

-continued

```
        115                 120                 125

Pro Gly Glu Gly Val Pro Gly Ala Gly Ser Gly Asp Gln Met Met Leu
    130                 135                 140

Pro Trp Pro Ala Val Ala Leu Ser Gly Val Pro Gly Val Gly Val Pro
145                 150                 155                 160

Gly Val Gly Val Pro Gly Ala Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Glu Gly
        195                 200                 205

Val Pro Gly Ala Gly Ser Gly Asp Gln Met Met Leu Pro Trp Pro Ala
    210                 215                 220

Val Ala Leu Ser Gly Val Pro Gly Val Gly Val Pro Gly Val Gly Val
225                 230                 235                 240

Pro Gly Ala Gly Val Pro Gly Val Gly Val Pro Gly Val Gly Val Pro
                245                 250                 255

Gly Val Gly Val Pro Gly Val Gly Val Pro Gly Val Gly Val Pro Gly
            260                 265                 270

Val Gly Val Pro Gly Val Gly Val Pro Gly Glu Gly Val Pro Gly Ala
        275                 280                 285

Gly Ser Gly Asp Gln Met Met Leu Pro Trp Pro Ala Val Ala Leu Ser
    290                 295                 300

Gly Val Pro Gly Val Gly Val Pro Gly Val Gly Val Pro Gly Ala Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Val Gly Val Pro Gly Glu Gly Val Pro Gly Ala Gly Val Pro Gly
        355                 360                 365

Val Gly Val Pro Gly Val Gly Val Pro Gly Ala Gly Val Pro Gly Val
    370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
                405                 410                 415

Pro Gly Glu Gly Val Pro Gly Ala Gly Val Pro Gly Val Gly Val Pro
            420                 425                 430

Gly Val Gly Val Pro Gly Ala Gly Val Pro Gly Val Gly Val Pro Gly
        435                 440                 445

Val Gly Val Pro Gly Val Gly Val Pro Gly Val Gly Val Pro Gly Val
    450                 455                 460

Gly Val Pro Gly Val Gly Val Pro Gly Val Gly Val Pro Gly Glu Gly
465                 470                 475                 480

Val Pro Gly Ala Gly Val Pro Gly Val Gly Val Pro Gly Val Gly Val
                485                 490                 495

Pro Gly Ala Gly Val Pro Gly Val Gly Val Pro Gly Val Gly Val Pro
            500                 505                 510

Gly Val Gly Val Pro Gly Val Gly Val Pro Gly Val Gly Val Pro Gly
        515                 520                 525

Val Gly Val Pro Gly Val Gly Val Pro Gly Glu Gly Val Pro Gly Ala
    530                 535                 540
```

```
Gly Val Pro Gly Val Gly Val Pro Gly Val Gly Val Pro Gly Ala Gly
545                 550                 555                 560

Val Pro Gly Val Gly Val Pro Gly Val Gly Val Pro Gly Val Gly Val
                565                 570                 575

Pro Gly Val Gly Val Pro Gly Val Gly Val Pro Gly Val Gly Val Pro
            580                 585                 590

Gly Val Gly Val Pro Gly Glu Gly Val Pro Gly Ala Gly Ser Gly Gly
        595                 600                 605

Ser Lys Gly Ser Ser Gly Val Pro Gly Val Gly Val Pro Gly Val Gly
    610                 615                 620

Val Pro Gly Ala Gly Val Pro Gly Val Gly Val Pro Gly Val Gly Val
625                 630                 635                 640

Pro Gly Val Gly Val Pro Gly Val Gly Val Pro Gly Val Gly Val Pro
                645                 650                 655

Gly Val Gly Val Pro Gly Val Gly Val Pro Gly Glu Gly Val Pro Gly
            660                 665                 670

Ala Gly Ser Gly Gly Ser Lys Gly Ser Ser Gly Val Pro Gly Val Gly
        675                 680                 685

Val Pro Gly Val Gly Val Pro Gly Ala Gly Val Pro Gly Val Gly Val
    690                 695                 700

Pro Gly Val Gly Val Pro Gly Val Gly Val Pro Gly Val Gly Val Pro
705                 710                 715                 720

Gly Val Gly Val Pro Gly Val Gly Val Pro Gly Val Gly Val Pro Gly
                725                 730                 735

Glu Gly Val Pro Gly Ala Gly Ser Gly Gly Ser Lys Gly Ser Ser Gly
            740                 745                 750

Val Pro Gly Val Gly Val Pro Gly Val Gly Val Pro Gly Ala Gly Val
        755                 760                 765

Pro Gly Val Gly Val Pro Gly Val Gly Val Pro Gly Val Gly Val Pro
    770                 775                 780

Gly Val Gly Val Pro Gly Val Gly Val Pro Gly Val Gly Val Pro Gly
785                 790                 795                 800

Val Gly Val Pro Gly Glu Gly Val Pro Gly Ala Gly Ser Gly Gly Ser
                805                 810                 815

Lys Gly Ser Ser Gly Val Pro Gly Trp Leu Asp Ser Leu Glu Phe Ile
            820                 825                 830

Ala
```

<210> SEQ ID NO 2
<211> LENGTH: 833
<212> TYPE: PRT
<213> ORGANISM: Artificial Sequence
<220> FEATURE:
<223> OTHER INFORMATION: conELP

<400> SEQUENCE: 2

```
Met Gly His Gly Val Gly Val Pro Gly Val Gly Val Pro Gly Ala Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Glu Gly Val Pro Gly Ala Gly Ser Gly Asp
    50                  55                  60
```

-continued

```
Gly Met Met Leu Pro Trp Pro Ala Val Ala Leu Ser Gly Val Pro Gly
65                  70                  75                  80

Val Gly Val Pro Gly Val Gly Val Pro Gly Ala Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
        115                 120                 125

Pro Gly Glu Gly Val Pro Gly Ala Gly Ser Gly Asp Gly Met Met Leu
    130                 135                 140

Pro Trp Pro Ala Val Ala Leu Ser Gly Val Pro Gly Val Gly Val Pro
145                 150                 155                 160

Gly Val Gly Val Pro Gly Ala Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Glu Gly
        195                 200                 205

Val Pro Gly Ala Gly Ser Gly Asp Gly Met Met Leu Pro Trp Pro Ala
    210                 215                 220

Val Ala Leu Ser Gly Val Pro Gly Val Gly Val Pro Gly Val Gly Val
225                 230                 235                 240

Pro Gly Ala Gly Val Pro Gly Val Gly Val Pro Gly Val Gly Val Pro
                245                 250                 255

Gly Val Gly Val Pro Gly Val Gly Val Pro Gly Val Gly Val Pro Gly
            260                 265                 270

Val Gly Val Pro Gly Val Gly Val Pro Gly Glu Gly Val Pro Gly Ala
        275                 280                 285

Gly Ser Gly Asp Gly Met Met Leu Pro Trp Pro Ala Val Ala Leu Ser
    290                 295                 300

Gly Val Pro Gly Val Gly Val Pro Gly Val Gly Val Pro Gly Ala Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Val Gly Val Pro Gly Glu Gly Val Pro Gly Ala Gly Val Pro Gly
        355                 360                 365

Val Gly Val Pro Gly Val Gly Val Pro Gly Ala Gly Val Pro Gly Val
    370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
                405                 410                 415

Pro Gly Glu Gly Val Pro Gly Ala Gly Val Pro Gly Val Gly Val Pro
            420                 425                 430

Gly Val Gly Val Pro Gly Ala Gly Val Pro Gly Val Gly Val Pro Gly
        435                 440                 445

Val Gly Val Pro Gly Val Gly Val Pro Gly Val Gly Val Pro Gly Val
    450                 455                 460

Gly Val Pro Gly Val Gly Val Pro Gly Val Gly Val Pro Gly Glu Gly
465                 470                 475                 480

Val Pro Gly Ala Gly Val Pro Gly Val Gly Val Pro Gly Val Gly Val
```

-continued

```
                485                 490                 495

Pro Gly Ala Gly Val Pro Gly Val Gly Val Pro Gly Val Gly Val Pro
            500                 505                 510

Gly Val Gly Val Pro Gly Val Gly Val Pro Gly Val Gly Val Pro Gly
        515                 520                 525

Val Gly Val Pro Gly Val Gly Val Pro Gly Glu Gly Val Pro Gly Ala
    530                 535                 540

Gly Val Pro Gly Val Gly Val Pro Gly Val Gly Val Pro Gly Ala Gly
545                 550                 555                 560

Val Pro Gly Val Gly Val Pro Gly Val Gly Val Pro Gly Val Gly Val
                565                 570                 575

Pro Gly Val Gly Val Pro Gly Val Gly Val Pro Gly Val Gly Val Pro
            580                 585                 590

Gly Val Gly Val Pro Gly Glu Gly Val Pro Gly Ala Gly Ser Gly Gly
        595                 600                 605

Ser Gly Gly Ser Ser Gly Val Pro Gly Val Gly Val Pro Gly Val Gly
    610                 615                 620

Val Pro Gly Ala Gly Val Pro Gly Val Gly Val Pro Gly Val Gly Val
625                 630                 635                 640

Pro Gly Val Gly Val Pro Gly Val Gly Val Pro Gly Val Gly Val Pro
                645                 650                 655

Gly Val Gly Val Pro Gly Val Gly Val Pro Gly Glu Gly Val Pro Gly
            660                 665                 670

Ala Gly Ser Gly Gly Ser Gly Gly Ser Ser Gly Val Pro Gly Val Gly
        675                 680                 685

Val Pro Gly Val Gly Val Pro Gly Ala Gly Val Pro Gly Val Gly Val
    690                 695                 700

Pro Gly Val Gly Val Pro Gly Val Gly Val Pro Gly Val Gly Val Pro
705                 710                 715                 720

Gly Val Gly Val Pro Gly Val Gly Val Pro Gly Val Gly Val Pro Gly
                725                 730                 735

Glu Gly Val Pro Gly Ala Gly Ser Gly Gly Ser Gly Gly Ser Ser Gly
            740                 745                 750

Val Pro Gly Val Gly Val Pro Gly Val Gly Val Pro Gly Ala Gly Val
        755                 760                 765

Pro Gly Val Gly Val Pro Gly Val Gly Val Pro Gly Val Gly Val Pro
    770                 775                 780

Gly Val Gly Val Pro Gly Val Gly Val Pro Gly Val Gly Val Pro Gly
785                 790                 795                 800

Val Gly Val Pro Gly Glu Gly Val Pro Gly Ala Gly Ser Gly Gly Ser
                805                 810                 815

Gly Gly Ser Ser Gly Val Pro Gly Trp Leu Asp Ser Leu Glu Phe Ile
            820                 825                 830

Ala


<210> SEQ ID NO 3
<211> LENGTH: 12
<212> TYPE: PRT
<213> ORGANISM: Artificial Sequence
<220> FEATURE:
<223> OTHER INFORMATION: Q-block sequence

<400> SEQUENCE: 3

Asp Gln Met Met Leu Pro Trp Pro Ala Val Ala Leu
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: Q-block sequence

<400> SEQUENCE: 4

Trp Gln His Lys Ile Asp Leu Arg Tyr Asn Gly Ala
1 5 10

<210> SEQ ID NO 5
<211> LENGTH: 12
<212> TYPE: PRT
<213> ORGANISM: Artificial Sequence
<220> FEATURE:
<223> OTHER INFORMATION: Q-block sequence

<400> SEQUENCE: 5

Ser Gln His Pro Leu Pro Trp Pro Val Leu Met Leu
1 5 10

<210> SEQ ID NO 6
<211> LENGTH: 12
<212> TYPE: PRT
<213> ORGANISM: Artificial Sequence
<220> FEATURE:
<223> OTHER INFORMATION: Q-block sequence

<400> SEQUENCE: 6

Glu Gln Phe Pro Ile Ala Phe Pro Arg Tyr Ser Ile
1 5 10

<210> SEQ ID NO 7
<211> LENGTH: 12
<212> TYPE: PRT
<213> ORGANISM: Artificial Sequence
<220> FEATURE:
<223> OTHER INFORMATION: Q-block sequence

<400> SEQUENCE: 7

Ser Glu Gln His Leu Leu Lys Trp Pro Pro Trp His
1 5 10

<210> SEQ ID NO 8
<211> LENGTH: 12
<212> TYPE: PRT
<213> ORGANISM: Artificial Sequence
<220> FEATURE:
<223> OTHER INFORMATION: Q-block sequence

<400> SEQUENCE: 8

Trp Gln Ile Pro Val Asp Trp Pro Pro Leu Pro Pro
1 5 10

<210> SEQ ID NO 9
<211> LENGTH: 12
<212> TYPE: PRT
<213> ORGANISM: Artificial Sequence
<220> FEATURE:
<223> OTHER INFORMATION: Q-block sequence

<400> SEQUENCE: 9

Asp Gln Trp Met Met Ala Trp Pro Ser Leu Thr Leu
1 5 10

<210> SEQ ID NO 10
<211> LENGTH: 12
<212> TYPE: PRT
<213> ORGANISM: Artificial Sequence
<220> FEATURE:
<223> OTHER INFORMATION: Q-block sequence

<400> SEQUENCE: 10

```
Ser Gln Ile Pro Met Ala Trp Pro Leu Leu Ser Leu
1               5                   10
```

<210> SEQ ID NO 11
<211> LENGTH: 5
<212> TYPE: PRT
<213> ORGANISM: Artificial Sequence
<220> FEATURE:
<223> OTHER INFORMATION: K-block sequence

<400> SEQUENCE: 11

```
Gly Ser Lys Gly Ser
1               5
```

<210> SEQ ID NO 12
<211> LENGTH: 5
<212> TYPE: PRT
<213> ORGANISM: Artificial Sequence
<220> FEATURE:
<223> OTHER INFORMATION: spacer sequences
<220> FEATURE:
<221> NAME/KEY: MISC_FEATURE
<222> LOCATION: (4)..(4)
<223> OTHER INFORMATION: can independently be selected from any proteogenic amino acid except Pro

<400> SEQUENCE: 12

```
Val Pro Gly Xaa Gly
1               5
```

<210> SEQ ID NO 13
<211> LENGTH: 55
<212> TYPE: PRT
<213> ORGANISM: Artificial Sequence
<220> FEATURE:
<223> OTHER INFORMATION: spacer sequence multimer

<400> SEQUENCE: 13

```
Val Pro Gly Val Gly Val Pro Gly Ala Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Glu Gly Val Pro Gly Ala Gly
    50                  55
```

<210> SEQ ID NO 14
<211> LENGTH: 60
<212> TYPE: PRT
<213> ORGANISM: Artificial Sequence
<220> FEATURE:
<223> OTHER INFORMATION: spacer sequence multimer

<400> SEQUENCE: 14

```
Val Pro Gly Val Gly Val Pro Gly Val Gly Val Pro Gly Ala Gly Val
1               5                   10                  15
```

```
Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Glu Gly Val Pro Gly Ala Gly
    50                  55                  60


<210> SEQ ID NO 15
<211> LENGTH: 5
<212> TYPE: PRT
<213> ORGANISM: Artificial Sequence
<220> FEATURE:
<223> OTHER INFORMATION: Control sequence

<400> SEQUENCE: 15

Gly Ser Gly Gly Ser
1               5


<210> SEQ ID NO 16
<211> LENGTH: 861
<212> TYPE: PRT
<213> ORGANISM: Artificial Sequence
<220> FEATURE:
<223> OTHER INFORMATION: hELP(4Tg-4Tg)

<400> SEQUENCE: 16

Met Gly His Gly Val Gly Val Pro Gly Val Gly Val Pro Gly Ala Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Glu Gly Val Pro Gly Ala Gly Ser Gly Asp
    50                  55                  60

Gln Met Met Leu Pro Trp Pro Ala Val Ala Leu Ser Gly Val Pro Gly
65                  70                  75                  80

Val Gly Val Pro Gly Val Gly Val Pro Gly Ala Gly Val Pro Gly Val
                85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
        115                 120                 125

Pro Gly Glu Gly Val Pro Gly Ala Gly Ser Gly Asp Gln Met Met Leu
    130                 135                 140

Pro Trp Pro Ala Val Ala Leu Ser Gly Val Pro Gly Val Gly Val Pro
145                 150                 155                 160

Gly Val Gly Val Pro Gly Ala Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Glu Gly
        195                 200                 205

Val Pro Gly Ala Gly Ser Gly Asp Gln Met Met Leu Pro Trp Pro Ala
    210                 215                 220

Val Ala Leu Ser Gly Val Pro Gly Val Gly Val Pro Gly Val Gly Val
225                 230                 235                 240

Pro Gly Ala Gly Val Pro Gly Val Gly Val Pro Gly Val Gly Val Pro
                245                 250                 255
```

-continued

```
Gly Val Gly Val Pro Gly Val Gly Val Pro Gly Val Gly Val Pro Gly
            260                 265                 270

Val Gly Val Pro Gly Val Gly Val Pro Gly Glu Gly Val Pro Gly Ala
        275                 280                 285

Gly Ser Gly Asp Gln Met Met Leu Pro Trp Pro Ala Val Ala Leu Ser
    290                 295                 300

Gly Val Pro Gly Val Gly Val Pro Gly Val Gly Val Pro Gly Ala Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
            340                 345                 350

Gly Val Gly Val Pro Gly Glu Gly Val Pro Gly Ala Gly Val Pro Gly
        355                 360                 365

Val Gly Val Pro Gly Val Gly Val Pro Gly Ala Gly Val Pro Gly Val
    370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
                405                 410                 415

Pro Gly Glu Gly Val Pro Gly Ala Gly Val Pro Gly Val Gly Val Pro
            420                 425                 430

Gly Val Gly Val Pro Gly Ala Gly Val Pro Gly Val Gly Val Pro Gly
        435                 440                 445

Val Gly Val Pro Gly Val Gly Val Pro Gly Val Gly Val Pro Gly Val
    450                 455                 460

Gly Val Pro Gly Val Gly Val Pro Gly Val Gly Val Pro Gly Glu Gly
465                 470                 475                 480

Val Pro Gly Ala Gly Val Pro Gly Val Gly Val Pro Gly Val Gly Val
                485                 490                 495

Pro Gly Ala Gly Val Pro Gly Val Gly Val Pro Gly Val Gly Val Pro
            500                 505                 510

Gly Val Gly Val Pro Gly Val Gly Val Pro Gly Val Gly Val Pro Gly
        515                 520                 525

Val Gly Val Pro Gly Val Gly Val Pro Gly Glu Gly Val Pro Gly Ala
    530                 535                 540

Gly Val Pro Gly Val Gly Val Pro Gly Val Gly Val Pro Gly Ala Gly
545                 550                 555                 560

Val Pro Gly Val Gly Val Pro Gly Val Gly Val Pro Gly Val Gly Val
                565                 570                 575

Pro Gly Val Gly Val Pro Gly Val Gly Val Pro Gly Val Gly Val Pro
            580                 585                 590

Gly Val Gly Val Pro Gly Glu Gly Val Pro Gly Ala Gly Ser Gly Asp
        595                 600                 605

Gln Met Met Leu Pro Trp Pro Ala Val Ala Leu Ser Gly Val Pro Gly
    610                 615                 620

Val Gly Val Pro Gly Val Gly Val Pro Gly Ala Gly Val Pro Gly Val
625                 630                 635                 640

Gly Val Pro Gly Val Gly Val Pro Gly Val Gly Val Pro Gly Val Gly
                645                 650                 655

Val Pro Gly Val Gly Val Pro Gly Val Gly Val Pro Gly Val Gly Val
            660                 665                 670
```

-continued

```
Pro Gly Glu Gly Val Pro Gly Ala Gly Ser Gly Asp Gln Met Met Leu
        675                 680                 685

Pro Trp Pro Ala Val Ala Leu Ser Gly Val Pro Gly Val Gly Val Pro
    690                 695                 700

Gly Val Gly Val Pro Gly Ala Gly Val Pro Gly Val Gly Val Pro Gly
705                 710                 715                 720

Val Gly Val Pro Gly Val Gly Val Pro Gly Val Gly Val Pro Gly Val
                725                 730                 735

Gly Val Pro Gly Val Gly Val Pro Gly Val Gly Val Pro Gly Glu Gly
            740                 745                 750

Val Pro Gly Ala Gly Ser Gly Asp Gln Met Met Leu Pro Trp Pro Ala
        755                 760                 765

Val Ala Leu Ser Gly Val Pro Gly Val Gly Val Pro Gly Val Gly Val
    770                 775                 780

Pro Gly Ala Gly Val Pro Gly Val Gly Val Pro Gly Val Gly Val Pro
785                 790                 795                 800

Gly Val Gly Val Pro Gly Val Gly Val Pro Gly Val Gly Val Pro Gly
                805                 810                 815

Val Gly Val Pro Gly Val Gly Val Pro Gly Glu Gly Val Pro Gly Ala
            820                 825                 830

Gly Ser Gly Asp Gln Met Met Leu Pro Trp Pro Ala Val Ala Leu Ser
        835                 840                 845

Gly Val Pro Gly Trp Leu Asp Ser Leu Glu Phe Ile Ala
    850                 855                 860
```

HEMOSTATIC ELASTIN-LIKE POLYPEPTIDES

CROSS-REFERENCE TO RELATED APPLICATIONS

This is the US National Stage of International Patent Application No. PCT/EP2021/072863, filed Aug. 17, 2021, which claims the priority of European Patent Application No. EP20191629, filed Aug. 18, 2020, the contents of which are incorporated by reference herein in their entirety.

The present invention relates to a hemostatic elastin-like polypeptide comprising a glutamine embedded in a Q-block sequence and, optionally, a lysine embedded in a K-block sequence. Under physiological conditions, the Q-block sequence and the K-block sequence are recognized by human transglutaminase factor XIIIa and crosslinked with fibrin networks. The present invention also relates to the medical use of the polypeptide, to a nucleic acid sequence encoding the polypeptide, to an expression vector comprising the nucleic acid sequence, and to a cell carrying the nucleic acid sequence or the expression vector.

BACKGROUND OF THE INVENTION

Severe trauma is a major cause of death among individuals 45 years of age and younger, and is projected to account for as many as 8.4 million deaths per year in 2020. Many of these deaths are caused by failure to achieve hemostasis. In cases of severe bleeding, clotting factors are rapidly depleted at the site of injury, leading to a condition known as trauma-induced coagulopathy (TIC) in as many as 25% of trauma patients, with an associated increase in mortality.

Hemostasis occurs in two phases, the primary phase of which involves activation and aggregation of circulating platelets at the injury site, forming a platelet plug. In the secondary phase, fibrin (Fb) is polymerized, forming an insoluble protein hydrogel (i.e. clot) that provides structural support and hinders blood flow. In this secondary phase, Fb networks form when activated thrombin cleaves fibrinopeptides from the precursor protein fibrinogen (Fg), revealing sequences known as knobs A and B. The knobs non-covalently bind to sites referred to as holes A and B on the distal ends of neighbouring Fb/Fg, allowing Fb to self-associate in a half-staggered conformation and form protofibrils. These protofibrils then bundle together to form fibres and eventually an insoluble Fb network. Fb networks are subsequently stabilized through covalent cross-links formed by a reaction between lysine and glutamine residues catalysed by activated clotting-associated transglutaminase, FXIIIa, and further stiffened through contractile forces exerted by platelets distributed throughout the network. Fb and FXIIIa are therefore both important players in hemostasis and represent valid molecular targets for hemostatic control systems.

Targeting Fb with synthetic systems is challenging because of the difficulty in obtaining specific high-affinity binders that discriminate between gelled Fb and circulating Fg. Since Fb clots and soluble Fg share sequence and structural homology, there are only a small number of conformational epitopes that can serve as a basis for molecular discrimination. Nonetheless, phage display has been used successfully to isolate Fb-specific binders. This has led to the development of Fb-targeting hemostats based on grafting Fb-binding peptides or nanobodies onto synthetic polymers or particles that bind Fb and support clot formation in vivo. Alternatively, Fb has also been targeted through engagement of its endogenous hole a and b binding pockets by knob A and B mimics. Through appending of these peptide mimics to larger molecules, such as polyethylene glycol (PEG) polymers or proteins, various constructs have been realized which are able to alter the mechanical properties of Fb, modulate Fb network structure, or target delivery of therapeutics to Fb gels.

Based on the above-mentioned state of the art, the objective of the present invention is to provide means and methods to achieve hemostasis. This objective is attained by the subject-matter of the independent claims of the present specification.

SUMMARY OF THE INVENTION

A first aspect of the invention relates to a polypeptide comprising, a. a Q-block amino acid sequence selected from:

```
i.
                              (SEQ ID NO 003)
DQMMLPWPAVAL,

ii.
                              (SEQ ID NO 004)
WQHKIDLRYNGA,

iii.
                              (SEQ ID NO 005)
SQHPLPWPVLML,

iv.
                              (SEQ ID NO 006)
EQFPIAFPRYSI,

v.
                              (SEQ ID NO 007)
SEQHLLKWPPWH,

vi.
                              (SEQ ID NO 008)
WQIPVDWPPLPP,

vii.
                              (SEQ ID NO 009)
DQWMMAWPSLTL,
and/or

viii.
                              (SEQ ID NO 010)
SQIPMAWPLLSL,
```

b. a plurality of spacer amino acid sequences VPGXG (SEQ ID NO 012);

c. optionally, a K-block sequence comprising at least one lysine residue.

Each X within any one spacer amino acid sequence can be independently selected from any proteogenic amino acid except Pro.

A second aspect of the invention relates to a polypeptide according to the first aspect for use in treatment or prevention of impaired hemostasis, excessive bleeding or coagulopathy.

A third aspect of the invention relates to a nucleic acid sequence encoding the polypeptide according to the first aspect.

Another aspect of the invention relates to an expression vector comprising the nucleic acid sequence according to the third aspect.

Yet another aspect of the invention relates to an isolated cell comprising the nucleic acid sequence according to the third aspect or the expression vector according to the fourth aspect of the invention.

DETAILED DESCRIPTION OF THE INVENTION

Terms and Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 4th ed. (2012) Cold Spring Harbor Laboratory Press, Cold Spring Harbor, N.Y. and Ausubel et al., Short Protocols in Molecular Biology (2002) 5th Ed, John Wiley & Sons, Inc.) and chemical methods.

The term ELP in the context of the present specification relates to elastin-like polypeptide.

The term Fb in the context of the present specification relates to fibrin.

The term hELP in the context of the present specification relates to hemostatic ELP.

The term polypeptide in the context of the present specification relates to a molecule consisting of 30 or more amino acids that form a linear chain wherein the amino acids are connected by peptide bonds. The amino acid sequence of a polypeptide may represent the amino acid sequence of a whole (as found physiologically) protein or fragments thereof. The term "polypeptides" and "protein" are used interchangeably herein and include proteins and fragments thereof. Polypeptides are disclosed herein as amino acid residue sequences.

The term peptide in the context of the present specification relates to a molecule consisting of up to 50 amino acids, in particular 8 to 30 amino acids, more particularly 8 to 15 amino acids, that form a linear chain wherein the amino acids are connected by peptide bonds.

Amino acid residue sequences are given from amino to carboxyl terminus. Capital letters for sequence positions refer to L-amino acids in the one-letter code (Stryer, Biochemistry, $3^{rd}$ ed. p. 21). Lower case letters for amino acid sequence positions refer to the corresponding D- or (2R)-amino acids. Sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term specific binding in the context of the present invention refers to a property of ligands that bind to their target with a certain affinity and target specificity. The affinity of such a ligand is indicated by the dissociation constant of the ligand. A specifically reactive ligand has a dissociation constant of $\leq 10^{-7}$ mol/L when binding to its target, but a dissociation constant at least three orders of magnitude higher in its interaction with a molecule having a globally similar chemical composition as the target, but a different three-dimensional structure. Of note, the polymers according to the invention are covalently bound, so they do not have 'reversible' binding to Fb/Fg and therefore are not characterized by a dissociation constant. A relevant affinity can be formulated for the enzyme (FXIIIa) to the polymer, which is characterized by a Km value (Michelis-Menten constant) of the enzyme.

A polymer of a given group of monomers is a homopolymer (made up of a multiple of the same monomer; the monomer being a Q- or K-block sequence); a copolymer of a given selection of monomers is a heteropolymer constituted by monomers of at least two of the group.

As used herein, the term pharmaceutical composition refers to a compound of the invention, or a pharmaceutically acceptable salt thereof, together with at least one pharmaceutically acceptable carrier. In certain embodiments, the pharmaceutical composition according to the invention is provided in a form suitable for topical, parenteral or injectable administration.

As used herein, the term pharmaceutically acceptable carrier includes any solvents, dispersion media, coatings, surfactants, antioxidants, preservatives (for example, antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington: the Science and Practice of Pharmacy, ISBN 0857110624).

As used herein, the term treating or treatment of any condition, disease or disorder (e.g. impaired hemostasis) refers in one embodiment, to ameliorating the disease or disorder (e.g. slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. Methods for assessing treatment and/or prevention of disease are generally known in the art, unless specifically described hereinbelow.

The invention relates to an intrinsically disordered protein based on an elastin-like polypeptide (ELP) sequence that specifically binds fibrin and modulates its mechanical properties. The inventors designed hemostatic ELPs (hELPs) containing N- and C-terminal peptide tags by introducing glutamine and lysine residues at the N and C terminal ends of an ELP. The peptide tags (Q-block and K-block sequence) are selectivity recognized by human transglutaminase factor XIIIa, and covalently linked into fibrin networks via the natural coagulation cascade. Phase separation of hELPs above their lower critical solution temperature (LCST) led to stiffening and rescue of clot biophysical properties under simulated conditions of dilutive coagulopathy. In addition to phase-dependent stiffening, the resulting hELP-Fb networks exhibited resistance to plasmin degradation, reduced pore sizes, and accelerated gelation rate following initiation of clotting.

A first aspect of the invention relates to a polypeptide comprising, or consisting of, one or several of each of the following components:

a. a Q-block sequence selected from:

i. DQMMLPWPAVAL, (SEQ ID NO 003)

ii. WQHKIDLRYNGA, (SEQ ID NO 004)

iii. SQHPLPWPVLML, (SEQ ID NO 005)

iv. EQFPIAFPRYSI, (SEQ ID NO 006)

v. SEQHLLKWPPWH, (SEQ ID NO 007)

vi. WQIPVDWPPLPP, (SEQ ID NO 008)

vii. DQWMMAWPSLTL, and/or (SEQ ID NO 009)

viii. SQIPMAWPLLSL, (SEQ ID NO 010)

b. a plurality of spacer sequences of the sequence VPGXG (SEQ ID NO 012);

c. optionally, a K-block sequence comprising at least one lysine residue.

The "Guest Residue X of the Spacer Sequence

In principle, each X can independently be selected from any proteogenic amino acid except Pro.

In certain embodiments, each X is independently selected from Ala, Val and Glu.

In certain embodiments, the ratio of Ala:Val:Glu being used for X is 1-3 Ala:7-10 Val:1 Glu.

In certain embodiments, the ratio of Ala:Val:Glu being used for X is approximately 2:8:1 to 2:9:1.

The Ala:Val:Glu ratio and exact amino acid of the X residue is very flexible and general. Depending on how the temperature/pH responsiveness of the polymer is to be tuned, the ratios and ordering of X residues in the molecules can be different. The relative ratio of the X residues is considered important in determining the pH and temperature-induced phase transition of the molecule. In certain embodiments, any of the classical substitutions for Glu, Ala or Val could be made in a small number of cases. A classical substitution of Glu is Asp. A classical substitution of Ala is Gly, Val, Ser, Thr. A classical substitution of Val is Ala, Leu, Thr or lie. In certain embodiments, a small number of cases is less than 30%. In certain embodiments, a small number of cases is less than 20%. In certain embodiments, a small number of cases is less than 10%. In certain embodiments, a small number of cases is less than 5%.

The transition temperature of ELPs is determined both by their length and composition at the guest residue; so if the number of pentapeptides is too large, the length of the ELP may be too long to be practically expressible. There is a feasible zone of composition and length, that allows the ELPs to be expressible, and to transition at temperatures above room temperature but below, equal to, or not far above physiological temperature.

Typical length values for the polypeptides according to the invention include, but are not limited to 90-1,340 amino acids in length, which corresponds to molecular mass values of 10,000-150,000 grams/mole.

The X parameter (guest residue composition) does not influence the range of possible lengths. For a given X residue composition, both long or short ELPs can be made. However, solubility is an important aspect that is controlled by a combination of factors including guest residue composition, length, and buffer composition. For example, if hydrophobic guest residues are used, the length cannot be too long because they become insoluble in water and will not express in *E. coli*. (see below/next page for a discussion how this affects transition temp.).

In certain embodiments, the compound of the invention is characterized by a transition temperature between 27° C. to 47° C. In certain embodiments, the compound of the invention is characterized by a transition temperature between 32° C. to 42° C. In certain embodiments, the compound of the invention is characterized by a transition temperature between 34° C. to 40° C. In certain embodiments, the compound of the invention is characterized by a transition temperature between 35° C. to 39° C.

In certain embodiments, the compound of the invention is characterized by a transition temperature between 27° C. to 37° C. In certain embodiments, the compound of the invention is characterized by a transition temperature between 32° C. to 37° C. In certain embodiments, the compound of the invention is characterized by a transition temperature between 35° C. to 37° C.

In certain embodiments, the compound of the invention is characterized by a transition temperature between 37° C. to 47° C. In certain embodiments, the compound of the invention is characterized by a transition temperature between 37°

C. to 42° C. In certain embodiments, the compound of the invention is characterized by a transition temperature between 37° C. to 39° C.

The skilled person is aware that there are clear rules that can be followed to adjust the transition temperature. For example, adding more hydrophobic amino acids (A, I, L, M, F, W, Y or V) to the guest residue X position will lower the transition temp. Adding charged or hydrophilic amino acids (R. H, K, D, E, S, T, N, Q) will tend to increase the transition temperature. To determine the transition temperature, each composition is produced in *E. Coli* and tested with a cloud point assay, which is essentially an absorbance measurement as a function of temperature from ~15° C.-100° C. (See examples below, Method 2).

Without wanting to be bound by scientific hypothesis, the inventors propose that the actual spacer sequence is not very important, but that the defined ratio of Ala:Val:Glu being used for X is one way of solving the problem underlying the invention. The ratio of Ala:Val:Glu determines the phase separation in response to physiological temperature, in addition to the length of the polypeptide.

The inventors have designed hELPs with transition temperatures below 37° C., which drives aggregate/nanoparticle formation at physiological temperature.

Data obtained so far do not indicate a particular importance for all repeats to have the same sequence. They could all have different ratios/compositions of the X residues.

Q-Block Sequences

In certain embodiments, the polypeptide according to the invention comprises the Q-block sequence identified by SEQ ID NO 003. In certain particular embodiments, the polypeptide according to the invention consists of several Q-block sequences identified by SEQ ID NO 003, and additionally spacer sequences identified by SEQ ID NO 012.

In certain embodiments, the polypeptide according to the invention comprises the Q-block sequence identified by SEQ ID NO 004. In certain particular embodiments, the polypeptide according to the invention consists of several Q-block sequences identified by SEQ ID NO 004, and additionally spacer sequences identified by SEQ ID NO 012.

In certain embodiments, the polypeptide according to the invention comprises the Q-block sequence identified by SEQ ID NO 005. In certain particular embodiments, the polypeptide according to the invention consists of several Q-block sequences identified by SEQ ID NO 005, and additionally spacer sequences identified by SEQ ID NO 012.

In certain embodiments, the polypeptide according to the invention comprises the Q-block sequence identified by SEQ ID NO 006. In certain particular embodiments, the polypeptide according to the invention consists of several Q-block sequences identified by SEQ ID NO 006, and additionally spacer sequences identified by SEQ ID NO 012.

In certain embodiments, the polypeptide according to the invention comprises the Q-block sequence identified by SEQ ID NO 007. In certain particular embodiments, the polypeptide according to the invention consists of several Q-block sequences identified by SEQ ID NO 007, and additionally spacer sequences identified by SEQ ID NO 012.

In certain embodiments, the polypeptide according to the invention comprises the Q-block sequence identified by SEQ ID NO 008. In certain particular embodiments, the polypeptide according to the invention consists of several Q-block sequences identified by SEQ ID NO 008, and additionally spacer sequences identified by SEQ ID NO 012.

In certain embodiments, the polypeptide according to the invention comprises the Q-block sequence identified by SEQ ID NO 009. In certain particular embodiments, the polypeptide according to the invention consists of several Q-block sequences identified by SEQ ID NO 009, and additionally spacer sequences identified by SEQ ID NO 012.

In certain embodiments, the polypeptide according to the invention comprises the Q-block sequence identified by SEQ ID NO 010. In certain particular embodiments, the polypeptide according to the invention consists of several Q-block sequences identified by SEQ ID NO 010, and additionally spacer sequences identified by SEQ ID NO 012.

In certain embodiments, the polypeptide comprises two or more Q-block sequences.

In certain embodiments, the polypeptide comprises two or more of the same Q-block sequences.

In certain embodiments, the polypeptide comprises two or more different Q-block sequences.

In certain embodiments, the polypeptide comprises two or more Q-block sequences, spacer sequences, but no K-block sequences.

In certain particular embodiments of any of the aspects and general embodiments disclosed herein, the Q block sequence is DQMMLPWPAVAL (SEQ ID NO 003).

In certain embodiments, the polypeptide comprises 2 to 50 Q-block sequences. In certain embodiments, the polypeptide comprises 2 to 8 Q-block sequences. In certain embodiments, the polypeptide comprises 3 to 6 Q-block sequences. In certain embodiments, the polypeptide comprises 4 Q-block sequences.

In certain particular embodiments, the polypeptide essentially consists of Q-block sequences and spacer sequences only. The Q block sequences may be flanked by short (1-3, particularly 2 amino acids) framing sequences. In particular embodiments, these framing sequences are GS.

The framing sequences, particularly GS spacers, are typically used as inert and soluble 'flexible spacers' in protein engineering.

In more particular embodiments, the polypeptide essentially consists of Q-block sequences and spacer sequences only the polypeptide consists of

- an N-terminal Q tract described by (VPGXG)n-[(Q-block)-(VPGXG)n]m
- wherein the Q-block sequence is identified by SEQ ID NO: 3, and representative VPGXG repeat units are identified by SEQ ID NO: 12.
- a C-terminal Q tract described by -[(Q-block)-(VPGXG)n]m-(VPGXG)o
- wherein the Q-block sequence is identified by SEQ ID NO: 3, and representative VPGXG repeat units are identified by SEQ ID NO: 12
- a spacer sequence multimer [(VPGXG)n]p separating the N-terminal Q tract and the C-terminal Q-tract, wherein the representative VPGXG repeat units are identified by SEQ ID NO: 12, and wherein
  - each n independently from any other n is an integer from 8 to 14, particularly from 10 to 12;
  - each m independently from any other m is an integer from 2 to 8, particularly from 3 to 6, more particularly m is 4;
  - o is an integer from 0 to 10;
  - p is an integer from 3 to 6, particularly p is 4 or 5.

In an even more particular embodiment, the polypeptide is SEQ ID NO 16 or a sequence having at least 95% sequence identity thereto and at least 80% of the biological activity as defined elsewhere herein.

Q-Block and K-Block Sequences

In certain embodiments, the polypeptide comprises two or more Q-block sequences, spacer sequences, and K-block sequences.

The Q-block sequence and the K-block sequence are selectivity recognized and crosslinked by human transglutaminase factor XIIIa. Crosslinking may take place between two polypeptides of the invention (also named hELP) or between one polypeptide of the invention and a fibrin molecule. Thereby, the polypeptide of the invention is integrated into fibrin networks. Both, the Q-block sequence and the K-block sequence, may be crosslinked with fibrin.

In certain embodiments, the polypeptide essentially consists of a Q-block sequence, a K-block sequence, and a plurality of spacer sequences as described above. In certain embodiments, a Q-block sequence is at the N-terminus of the polypeptide, and a K-block-sequence is at the C-terminus of the polypeptide. In certain embodiments, a K-block sequence is at the N-terminus of the polypeptide, and a K-block-sequence is at the C-terminus of the polypeptide.

In certain embodiments, the polypeptide comprises a K-block sequence. In certain embodiments, the polypeptide comprises a K-block sequence GSKGS (SEQ ID NO 011). In certain embodiments, the polypeptide comprises two or more K-block sequences GSKGS (SEQ ID NO 011).

In certain embodiments, the polypeptide comprises 2 to 50 K-block sequences. In certain embodiments, the polypeptide comprises 2 to 8 K-block sequences. In certain embodiments, the polypeptide comprises 3 to 6 K-block sequences. In certain embodiments, the polypeptide comprises 4 K-block sequences.

In certain embodiments, the polypeptide comprises independently from each other 2 to 8 Q-block sequences and 2 to 8 K-block sequences. In certain embodiments, the polypeptide comprises independently from each other 3 to 6 Q-block sequences and 3 to 6 K-block sequences. In certain embodiments, the polypeptide comprises independently from each other 4 Q-block sequences and 4 K-block sequences.

In certain embodiments, the polypeptide essentially consists of Q-block sequences and spacer sequences. In certain embodiments, the polypeptide essentially consists of Q-block sequences, spacer sequences, and K-block sequences.

In certain embodiments, the polypeptide according to the invention consists of several Q-block sequences identified by SEQ ID NO 003, K-block sequences as identified in the present specification, and additionally spacer sequences identified by SEQ ID NO 012.

In certain embodiments, the polypeptide according to the invention consists of several Q-block sequences identified by SEQ ID NO 004, K-block sequences as identified in the present specification, and additionally spacer sequences identified by SEQ ID NO 012.

In certain embodiments, the polypeptide according to the invention consists of several Q-block sequences identified by SEQ ID NO 005, K-block sequences as identified in the present specification, and additionally spacer sequences identified by SEQ ID NO 012.

In certain embodiments, the polypeptide according to the invention consists of several Q-block sequences identified by SEQ ID NO 006, K-block sequences as identified in the present specification, and additionally spacer sequences identified by SEQ ID NO 012.

In certain embodiments, the polypeptide according to the invention consists of several Q-block sequences identified by SEQ ID NO 007, K-block sequences as identified in the present specification, and additionally spacer sequences identified by SEQ ID NO 012.

In certain embodiments, the polypeptide according to the invention consists of several Q-block sequences identified by SEQ ID NO 008, K-block sequences as identified in the present specification, and additionally spacer sequences identified by SEQ ID NO 012.

In certain embodiments, the polypeptide according to the invention consists of several Q-block sequences identified by SEQ ID NO 009, K-block sequences as identified in the present specification, and additionally spacer sequences identified by SEQ ID NO 012.

In certain embodiments, the polypeptide according to the invention consists of several Q-block sequences identified by SEQ ID NO 010, K-block sequences as identified in the present specification, and additionally spacer sequences identified by SEQ ID NO 012.

In certain embodiments, the spacer sequences form a contiguous amino acid chain without intervening sequences that are not Q-block sequences or K-block sequences. In other words, the spacer sequences are followed by further spacer sequences being only interrupted by Q-block sequences or K-block sequences. There are essentially no other components of the polypeptide than Q-block sequences, spacer sequences, and K-block sequences.

K and Q blocks numbers are not required to be the same. In certain embodiments, K and Q blocks are different in number.

In certain embodiments, the number of K and Q block sequences is the same.

In certain embodiments, each Q-block sequence and each K-block sequence are separated by at least 2 spacer sequences from any other Q-block and K-block sequence. In certain embodiments, each Q-block sequence and each K-block sequence are separated by at least 3 or 4 spacer sequences from any other Q-block and K-block sequence. In certain embodiments, each Q-block sequence and each K-block sequence are separated by 10 to 14 spacer sequences from any other Q-block and K-block sequence. In certain embodiments, each Q-block sequence and each K-block sequence are separated by 12 spacer sequences from any other Q-block and K-block sequence.

In certain embodiments, Q-block sequences and K-block sequences are mixed in their order, meaning that not all sequences of one kind are at the N-terminal end and the other kind of sequences at the C-terminal end. For example, one Q-block sequence may be followed by a K-block sequence and then another Q-block sequence may follow. In other words, it is a valid design to have Q-block sequences and K-block sequences adjacent to one another in the sequence.

In certain embodiments, all Q-block sequences comprised in the polypeptide are comprised within a Q sequence tract, and all K-block sequences are comprised within a K sequence tract.

In certain embodiments, the Q sequence tract is N terminal of the K sequence tract.

For the invention, it is not necessary for the Q-block sequence tract to be N-terminal and K-block sequence tract to be C-terminal.

In certain embodiments, the polypeptide comprises 50 to 1200 spacer sequences. In certain embodiments, the polypeptide comprises 90 to 250 spacer sequences. In certain embodiments, the polypeptide comprises 120 to 180 spacer sequences.

In certain embodiments, the Q sequence tract and the K sequence tract are separated by at least 30 spacer sequences. In certain embodiments, the Q sequence tract and the K sequence tract are separated by at least 40 spacer sequences. In certain embodiments, the Q sequence tract and the K sequence tract are separated by at least 50 spacer sequences.

In certain embodiments, spacer sequences are comprised in spacer sequence multimers comprising 6 to 15 spacer sequences, as a contiguous sequence. In certain embodiments, spacer sequences are comprised in spacer sequence multimers comprising 10 to 14 spacer sequences, as a contiguous sequence.

In certain embodiments, each Q block sequence is separated from any other Q block sequence by one spacer sequence multimer.

In certain embodiments, each K block sequence is separated from any other K block sequence by one spacer sequence multimer.

In certain embodiments, the Q sequence tract is separated from the K sequence tract by 3 to 5 spacer sequence multimers.

In certain embodiments, all spacer sequence multimers have the same sequence. In certain embodiments, the spacer sequence multimer sequence is or comprises the sequence VPGVGVP-GAGVPGVGVPGVGVPGVGVPGVGVPGVGVPGVGV PGVGVPGEGVPGAG (SEQ ID NO 013). In certain embodiments, the spacer sequence multimer sequence is or comprises the sequence VPGVGVPGVGVP-GAGVPGVGVPGVGVPGVGVPGVGVPGVGV PGVGVPGVGVPGEGVPGAG (SEQ ID NO 014).

In certain embodiments, the polypeptide comprises or essentially consists of an amino acid sequence characterized by more than (≥) 85% identity to the polypeptide sequence of SEQ ID NO 001, and is characterized by at least 85% biological activity of the polypeptide sequence of SEQ ID NO 001. In certain embodiments, the polypeptide comprises or essentially consists of an amino acid sequence characterized by ≥90% identity to the polypeptide sequence of SEQ ID NO 001, and is characterized by at least 85% biological activity of the polypeptide sequence of SEQ ID NO 001. In certain embodiments, the polypeptide comprises or essentially consists of an amino acid sequence characterized by ≥92% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by ≥94% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by ≥95% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by ≥96% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by ≥97% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by ≥98% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by ≥99% identity to the polypeptide sequence of SEQ ID NO 001, and is characterized by at least 85% biological activity of the polypeptide sequence of SEQ ID NO 001.

In certain embodiments, the polypeptide comprises or essentially consists of an amino acid sequence characterized by 100% identity to the polypeptide sequence of SEQ ID NO 001, and is characterized by at least 85% biological activity of the polypeptide sequence of SEQ ID NO 001.

Assay for Biological Activity

Rheological Measurements of protein of interest-containing Fb Clots: The mechanical properties of in vitro Fb clots containing 30, 20, 10, or 5 μM (μmol/L) protein of interest, 30 μM conELP, or an equal volume of HEPES buffer are assessed using an Anton Paar MCR 302 Rheometer with a cone-plate geometry (d=25 mm; 1° angle). To determine their oscillatory shear moduli, frequency sweep measurements are performed, whereby clotting solutions are prepared containing 1.5, 2.2, or 3.0 mg $mL^{-1}$ fibrinogen (Fg), protein of interest, conELP, or HEPES buffer, 20 mM $CaCl_2$, and 0.2 U $mL^{-1}$ Thrombin. Immediately upon the addition of Thrombin, 90 μL of the clot solution is transferred to the preheated Peltier plate of the rheometer at 22 or 37° C., the measuring cone is lowered onto the sample, and the cone is spun at 60 rpm for 5 seconds to ensure proper mixing and sample distribution. Silicone oil (t=100 cSt) is applied to the edges of the sample in order to prevent evaporation, and the clot is allowed to equilibrate for 1 hr, after which time a frequency sweep is performed from 0.1-3 Hz (γ=1%; previously determined to be within the Linear Viscoelastic Region (LVE) for this material) to determine the biological activity of the protein of interest. The output of the measurement is obtention of values for the storage (G') and loss (G") moduli of the material, parameters are well known in material science, relating to the material's stiffness (G') and viscosity (G"). These parameters are compared between hELPs/Fb gels and Fb alone; an increase in stiffness (G'), especially at low strain values (i.e., low force) is observed. In the absence of other parameters, the threshold for biological activity is an increase in G'>200 Pascals.

A second aspect of the invention relates to a polypeptide according to the first aspect for use in treatment or prevention of a condition selected from trauma, impaired hemostasis, excessive bleeding or coagulopathy.

In certain embodiments, the coagulopathy is dilutive (dilutional) coagulopathy or trauma-induced coagulopathy.

In addition to trauma-induced coagulopathy, the treatment according to the invention will also be useful in cases of internal bleeding where a patient's clotting response is insufficient due to the size of the wound, despite their having sufficient endogenous clotting factors present.

Dilutional Coagulopathy refers to the coagulopathy seen during massive transfusion for major trauma and/or haemorrhaging. Major trauma and haemorrhage cause coagulation abnormalities due to consumption of coagulation factors and platelets. Dilutional coagulopathy is due to dilution, along with consumption, of platelets during massive transfusion. Large volumes of crystalloid fluid used for resuscitation in these cases can also contribute to thrombocytopenia. Packed red blood cells contain few platelets when stored for over 24 hours, and the platelets that packed red blood cells do contain are typically damaged and removed from circulation upon transfusion. Thrombocytopenia with platelet levels between 50,000 and 75,000/$mm^3$ during massive transfusion should be treated with platelet concentrates. The number of units of packed red blood cells transfused does not accurately predict the degree of thrombocytopenia or the need for platelet transfusion.

Coagulopathy (also called a bleeding disorder) is a condition in which the blood's ability to coagulate (form clots) is impaired. Coagulopathy may cause uncontrolled internal or external bleeding. Left untreated, uncontrolled bleeding may cause damage to joints, muscles, or internal organs and may be life-threatening. Coagulopathy may be caused by reduced levels or absence of blood-clotting proteins, known as clotting factors or coagulation factors. Genetic disorders, such as haemophilia and Von Willebrand disease, can cause a reduction in clotting factors.

In certain embodiments, impaired haemostasis, excessive bleeding or coagulopathy is associated with or caused by a. a platelet disorder, a coagulation disorder, a defect in blood vessels, and/or thrombocytopenia,
b. excessive anticoagulation, particularly anticoagulation caused by administration of warfarin, heparin, or a direct oral anticoagulant (e.g., apixaban, edoxaban, rivaroxaban);
c. Liver disease (inadequate production of coagulation factors)
d. Von Willebrand disease,
e. Hemophilia
f. Trauma.

A more detailed description of excessive bleeding can be found at: msdmanuals.com/professional/hematology-and-oncology/hemostasis/excessive-bleeding.

A third aspect of the invention relates to a nucleic acid sequence encoding the polypeptide according to the invention as described in any of the aspects and embodiments laid out herein.

Another aspect of the invention relates to an expression vector comprising the nucleic acid sequence according to the third aspect. An expression vector or expression construct can be A fifth aspect of the invention relates to a cell comprising the nucleic acid sequence according to the third aspect or the expression vector according to the fourth aspect.

Medical Treatment, Dosage Forms and Salts

Similarly, within the scope of the present invention is a method or treating impaired hemostasis, excessive bleeding or coagulopathy in a patient in need thereof, comprising administering to the patient a polypeptide according to the above description.

Similarly, a dosage form for the prevention or treatment of impaired hemostasis, excessive bleeding or coagulopathy is provided, comprising a non-agonist ligand according to any of the above aspects or embodiments of the invention.

The skilled person is aware that any specifically mentioned drug may be present as a pharmaceutically acceptable salt of said drug. Pharmaceutically acceptable salts comprise the ionized drug and an oppositely charged counterion. Non-limiting examples of pharmaceutically acceptable anionic salt forms include acetate, benzoate, besylate, bitatrate, bromide, carbonate, chloride, citrate, edetate, edisylate, embonate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate, phosphate, diphosphate, salicylate, disalicylate, stearate, succinate, sulfate, tartrate, tosylate, triethiodide and valerate. Non-limiting examples of pharmaceutically acceptable cationic salt forms include aluminium, benzathine, calcium, ethylene diamine, lysine, magnesium, meglumine, potassium, procaine, sodium, tromethamine and zinc.

Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Topical administration is also within the scope of the advantageous uses of the invention. The skilled artisan is aware of a broad range of possible recipes for providing topical formulations, as exemplified by the content of Benson and Watkinson (Eds.), Topical and Transdermal Drug Delivery: Principles and Practice (1st Edition, Wiley 2011, ISBN-13: 978-0470450291); and Guy and Handcraft: Transdermal Drug Delivery Systems: Revised and Expanded ($2^{nd}$ Ed., CRC Press 2002, ISBN-13: 978-0824708610); Osborne and Amann (Eds.): Topical Drug Delivery Formulations ($1^{st}$ Ed. CRC Press 1989; ISBN-13: 978-0824781835).

Topical administration could be possible as two component precursor solutions in a double-barrelled syringe, which could be extruded onto topical wounds, or as an additive to wound dressings such as bandages.

Pharmaceutical Compositions and Administration

Another aspect of the invention relates to a pharmaceutical composition comprising a compound of the present invention, or a pharmaceutically acceptable salt thereof, and a pharmaceutically acceptable carrier. In further embodiments, the composition comprises at least two pharmaceutically acceptable carriers, such as those described herein.

In certain embodiments of the invention, the compound of the present invention is typically formulated into pharmaceutical dosage forms to provide an easily controllable dosage of the drug and to give the patient an elegant and easily handleable product.

In embodiments of the invention relating to topical uses of the compounds of the invention, the pharmaceutical composition is formulated in a way that is suitable for topical administration such as aqueous solutions, suspensions, ointments, creams, gels or sprayable formulations, e.g., for delivery by aerosol or the like, comprising the active ingredient together with one or more of solubilizers, stabilizers, tonicity enhancing agents, buffers and preservatives that are known to those skilled in the art.

The pharmaceutical composition can be formulated for oral administration, parenteral administration, or rectal administration. In addition, the pharmaceutical compositions of the present invention can be made up in a solid form (including without limitation capsules, tablets, pills, granules, powders or suppositories), or in a liquid form (including without limitation solutions, suspensions or emulsions).

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. In certain embodiments, the compounds of the invention may be administered in a single daily dose, or the total daily dosage may be administered in divided doses of two, three, or four times daily.

In certain embodiments, the pharmaceutical composition or combination of the present invention can be in unit dosage of about 1-1000 mg of active ingredient(s) for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The pharmaceutical compositions of the present invention can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. They may be produced by standard processes, for instance by conventional mixing, granulating, dissolving or lyophilizing processes. Many such procedures and methods for preparing pharmaceutical compositions are known in the art, see for example L. Lachman et al. The Theory and Practice of Industrial Pharmacy, 4th Ed, 2013 (ISBN 8123922892).

Wherever alternatives for single separable features such as, for example, an isotype protein or medical indication are laid out herein as "embodiments", it is to be understood that such alternatives may be combined freely to form discrete embodiments of the invention disclosed herein. Thus, any of the alternative embodiments for an isotype protein may be combined with any of the alternative embodiments of medical indication mentioned herein.

The invention is further illustrated by the following examples and figures, from which further embodiments and advantages can be drawn. These examples are meant to illustrate the invention but not to limit its scope.

DESCRIPTION OF THE FIGURES

FIG. 1 shows schematic representation of hELP design, and integration into Fb clots. (a) hELPs were designed as triblock copolymers containing a Q-block (DQMMLPWPAVAL (SEQ ID NO:3)), a phase separation block, and a K-block (GSKGS (SEQ ID NO: 11)). (b) Above the LCST, hELPs phase separate to form coacervates, which can be covalently cross-linked by FXIIIa. (c) Upon mixing with fibrinogen, thrombin and FXIII, hELP coacervates covalently integrate into Fb networks and improve mechanical strength in a phase-dependant manner, and also improve gelation kinetics, reduce the plasmin degradation rate, and reduce the Fb network pore size.

FIG. 5 shows in-vitro characterization of mechanical properties and thromboelastography of hELP-Fb clots. a) Average shear storage moduli of Fb gels containing either 30 μM hELP, conELP, or an equivalent volume of HEPES buffer. Gels were allowed to form between the cone and plate of the rheometer at either 22° C. or 37° C., after which a frequency sweep was performed from 0.1-3 Hz at 1% strain. The dotted line indicates the critical physiological threshold stiffness corresponding to the average shear storage modulus of the 2.2 mg $mL^{-1}$ Fb HEPES control gel. b) Strain sweeps from 0.1-100% (f=1 Hz) of 2.2 mg $mL^{-1}$ Fb gels containing 30 μM hELP, conELP, or HEPES buffer at 37° C. Data in all panels are shown as mean±SD (n=3) P<0.01, *P<0.001; one-way ANOVA with Tukey's post hoc test.

FIG. 12 shows SEQ ID NO: 1 with its specific domains annotated. Underlined text indicates the spacer/ELP repeats/VPGXG domain (SEQ ID NO: 12). Bold text indicates the Q block/transglutaminase inhibitor domain (SEQ ID NO: 3). Bold italic text indicates K-Block sequence (SEQ ID NO: 11) which is the portion deleted in SEQ ID NO: 16 and replaced with the Q block/transglutaminase inhibitor domain (SEQ ID NO: 3).

FIG. 13 shows SEQ ID NO: 16 with its specific domains annotated. Underlined text indicates the spacer/ELP repeats/VPGXG domain (SEQ ID NO: 12). Bold text indicates the Q block/transglutaminase inhibitor domain (SEQ ID NO: 3).

EXAMPLES

Example 1: Design and Characterization of Hemostatic ELPs (hELPs)

The inventors designed hELPs with an ABC triblock architecture (FIG. 1*a*). The repetitive ELP component present in all three blocks comprised 11 VPGXG (SEQ ID NO 012) pentapeptides with alanine, valine, and glutamic acid residues in guest positions at a ratio of 2:8:1 ($A_2V_8E_1$). The N-terminal hELP block, referred to as the Q-block, additionally contained 4 transglutaminase tags (FIG. 1*a*), each comprising a single glutamine residue embedded within a contextual sequence (DQMMLPWPAVAL (SEQ ID NO 003)). These transglutaminase tags were previously shown to be recognized with high-specificity by human FXIIIa. By embedding these FXIIIa-susceptible sequences in the broader hELP sequence, the inventors hypothesized that hELPs would selectively integrate into Fb networks at wound sites where FXIII is activated, while avoiding off-target interactions with soluble fibrinogen. The middle hELP block imparted phase separation ability and consisted of 4 consecutive $A_2V_8E_1$ units, totalling 48 pentapeptide repeats. This stimuli-responsive middle block triggered phase separation of hELPs in response to physiological temperature (37° C.). Finally, the C-terminus of hELPs contained 4 lysine blocks (K-block, GSKGS (SEQ ID NO 011)), which served as the complementary partner to glutamine in the reaction catalysed by FXIIIa. A control ELP (conELP) was also prepared with the same sequence as hELP, except that glutamine and lysine residues were mutated to glycine such that conELP was not cross-linked by FXIIIa.

Figure 2:
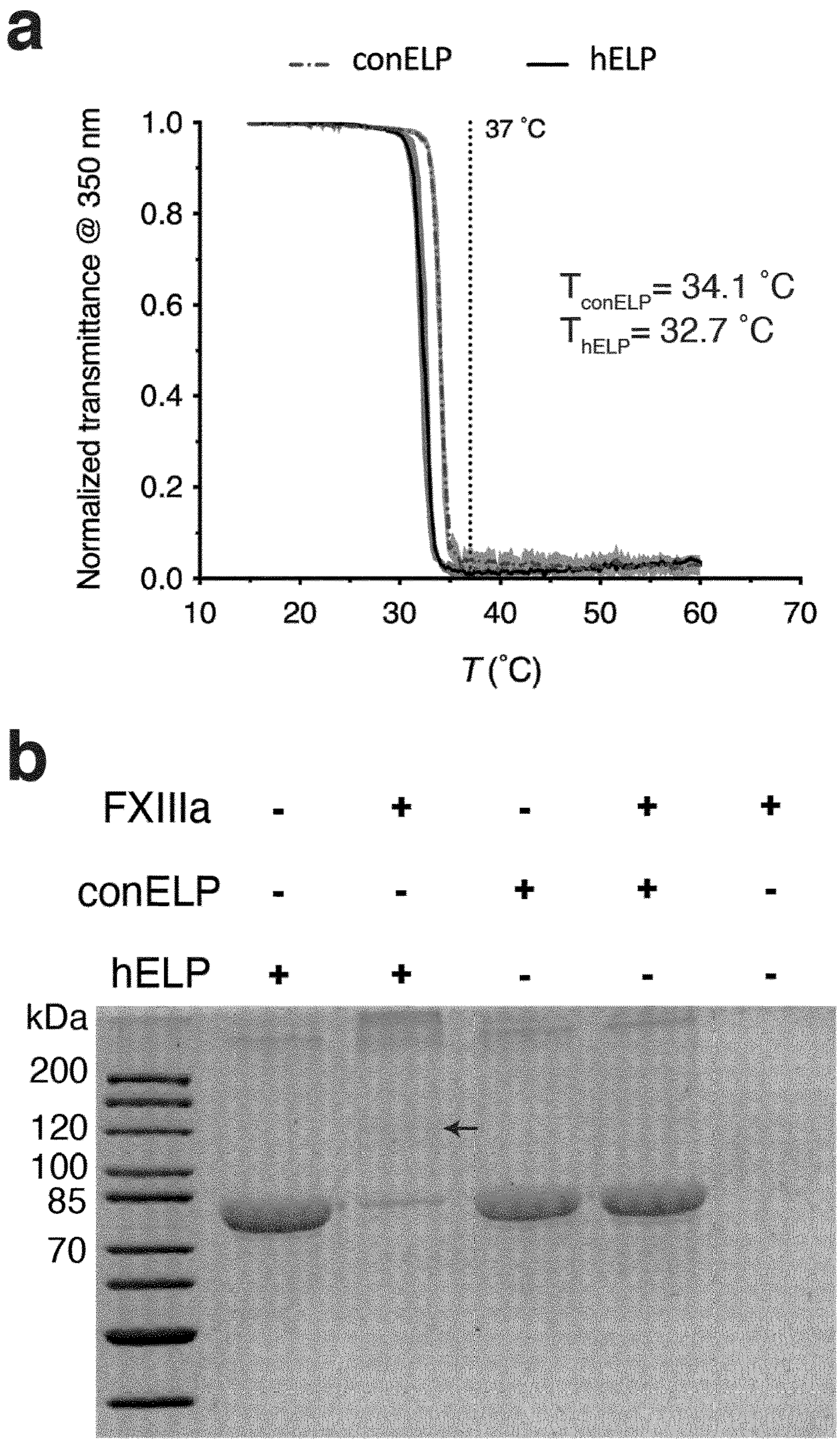
FIG. 2 shows cloud point and FXIIIa-mediated cross-linking of hELP and conELP. (a) Cloud points were determined for 30 μM solutions of hELP or conELP in 20/150 mM HEPES/NaCl+20 mM $CaCl_2$. Cloud points were defined as the temperature at which normalized transmittance fell below 0.5. Data shown are mean±SD (shaded area) (n=2) (b) SDS-PAGE gel following incubation of 50 μM hELP or conELP with 10 μg $mL^{-1}$ human FXIIIa for 1 hour at 37° C. The arrow indicates the position corresponding to hELP dimers.

The inventors cloned, expressed and purified hELPs and conELPs by inverse transition cycling (ITC), and measured LCSTs using a cloud point assay (C. Boutris et al., *Polymer (Guildf)*. 1997, 38, 2567.). At a working concentration of 30 μM, both hELP and conELP exhibited cloud points below 37° C. (32.7 and 34.1° C. respectively), indicating that both ELPs were aggregated at physiological temperature (FIG. 2*a*). Next, the inventors confirmed the functionality of the Q- and K-blocks by testing the ability of FXIIIa to cross-link hELP in the absence of Fg using SDS-PAGE (FIG. 2*b*). A reduction in intensity of the band corresponding to single hELP polymers (~69.5 kDa), and the appearance of bands of higher molecular weights corresponding to hELP dimers and multimers confirmed that FXIIIa was capable of cross-linking hELPs. Meanwhile, samples of conELP incubated with FXIIIa were not cross-linked. Molecular weights of hELPs and conELPs were confirmed by mass spectrometry.

Example 2: Integration of hELPs into Fb Networks

Figure 3:
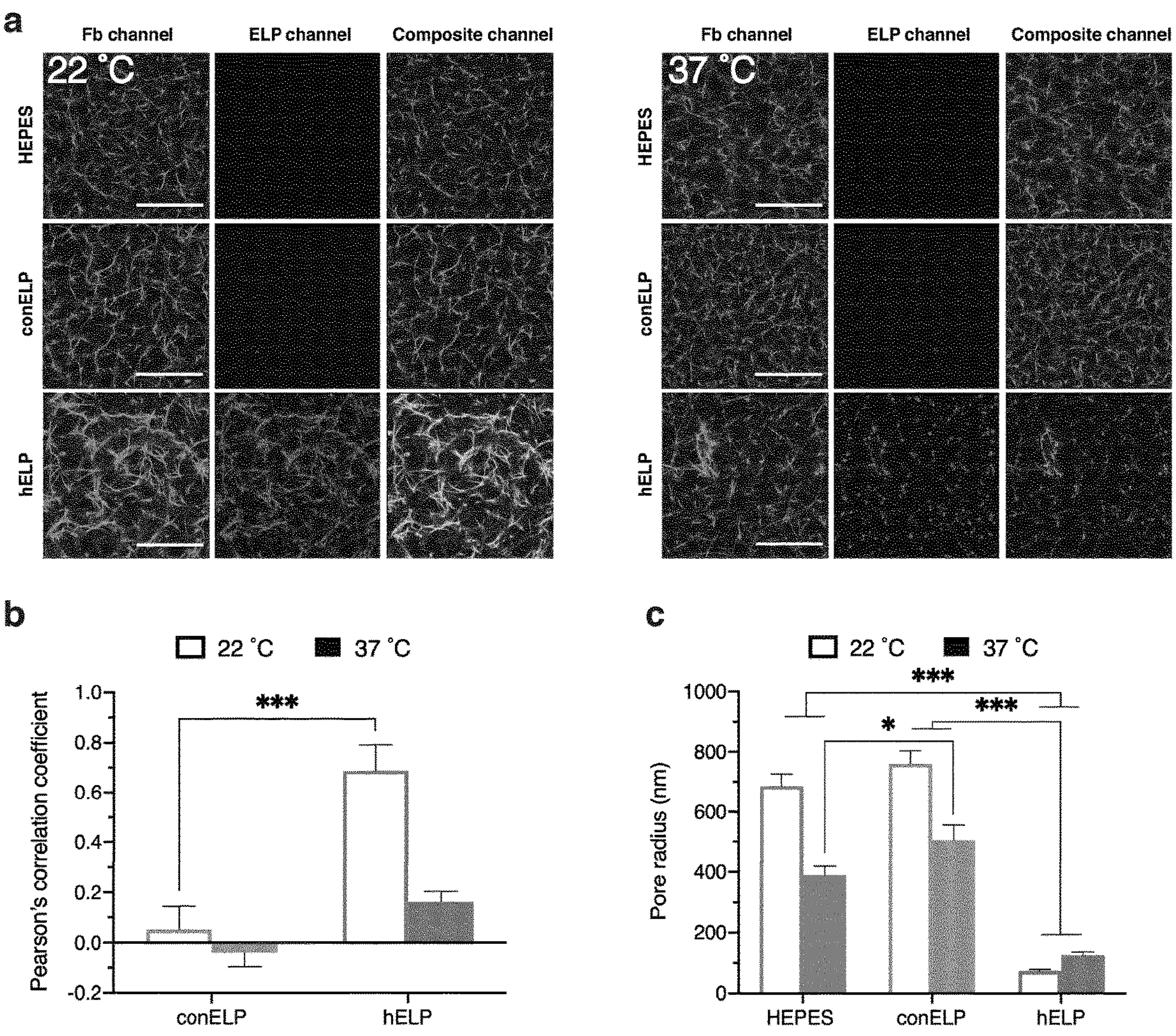
FIG. 3 shows characterizing structural morphology of hELP-Fb clots. (a) Two color confocal fluorescence microscopy of Fb clots formed at 22 or 37° C., with f-conELP, f-hELP or HEPES buffer as additives. Scale bars are 30 μm. (b) Comparison of Pearson's correlation coefficients quantifying spatial colocalization of signals from the Fb (green) or ELP (red) channels in confocal fluorescence images. (c) Pore sizing of Fb clots containing hELP, conELP, or HEPES buffer. Statistical significance was determined using one-way analysis of variance (ANOVA) with Tukey's Post Hoc test. *P<0.05, ***P<0.001. All data in panels b and c are shown as mean±SD (n=3).

The inventors N-terminally labelled hELPs and conELPs with Atto647-N-hydroxysuccinimide (red channel) and confirmed they were still cross-linked by FXIIIa. Fluorescent-hELPs (f-hELPs) or fluorescent-conELPs (f-conELPs) were then integrated into Fb clots spiked with 1% AlexaFluor 488-labelled fibrinogen (Fg-488, green channel). The inventors used two color confocal fluorescence microscopy to characterize hELP and Fb network morphology, degree of hELP and Fb colocalization, and the influence of hELP phase transition on clot architecture. At 22° C., all three clots (HEPES-Fb, conELP-Fb and hELP-Fb) resulted in well-defined Fb networks when imaged in the green Fb channel (FIG. 3*a*, left). When imaged in the red hELP channel, f-hELP fluorescence similarly showed an ordered network with high degree of spatial colocalization between hELP and Fb signals (FIG. 3*a*, left, hELP). The inventors observed little to no fluorescence intensity in the red channel when only HEPES buffer or f-conELP were added during formation of Fb networks (FIG. 3*a*, left, HEPES & conELP).

To quantify hELP and Fb spatial colocalization, the inventors used Coloc2 in ImageJ to calculate Pearson's correlation coefficients (PCC) (J. Adler, I. Parmryd, *Cytom. Part A* 2010, 77, 733.). For f-hELP-Fb clots at 22° C., a PCC between f-hELP and Fb channels of 0.69±0.1 indicated high spatial correlation. For f-conELP-Fb clots, a PCC value of 0.05±0.09 indicated no spatial correlation (FIG. 3*b*). These results demonstrate that when hELP is mixed with Fb and FXIIIa below the LCST, it is specifically cross-link and localizes to Fb fibers.

Figure 7:
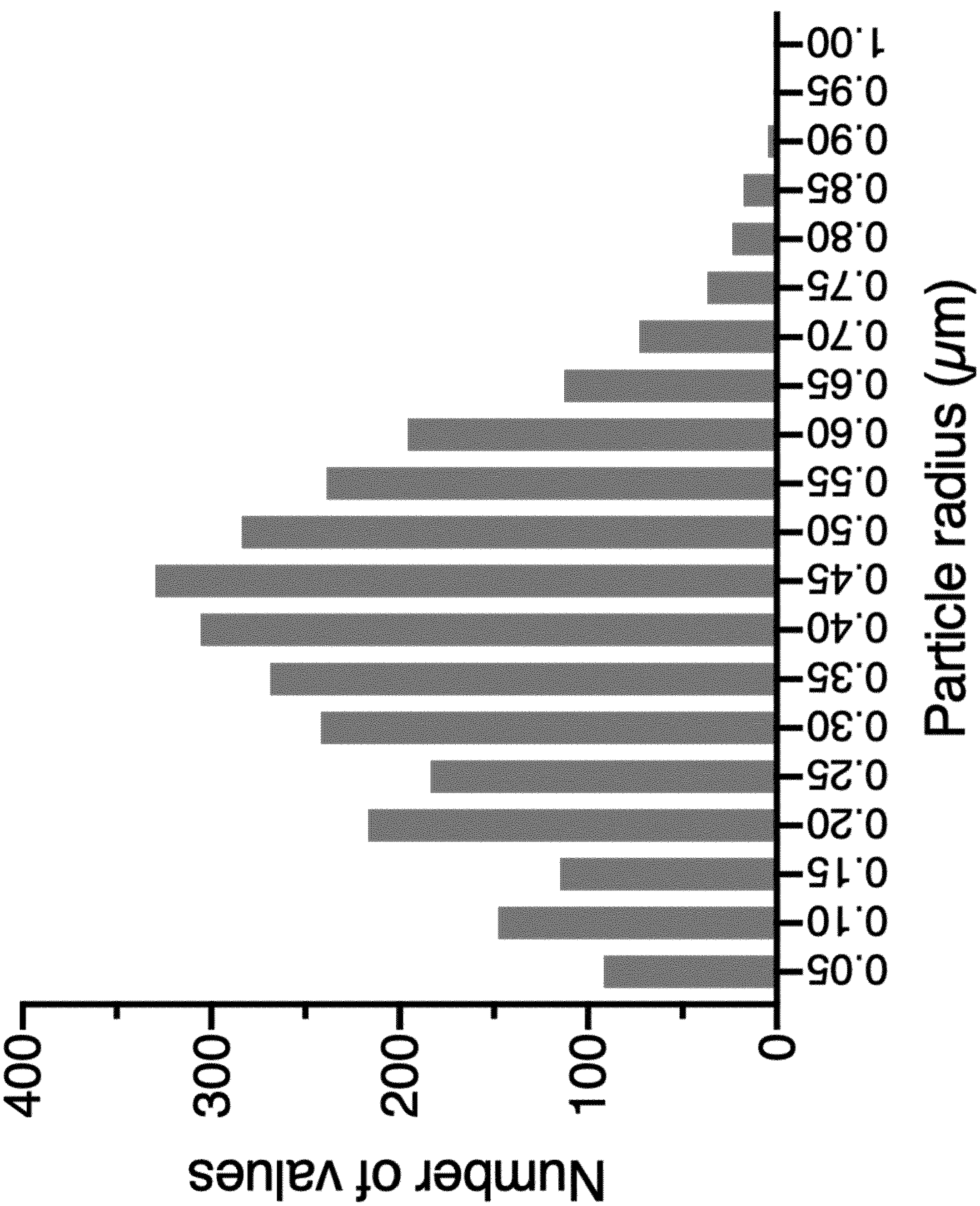
FIG. 7 shows hELP coacervate size distribution in 1.5 mg $mL^{-1}$ Fb clots formed at 37° C. Particle sizes were determined from images of three different hELP-containing Fb clots.

At 37° C., above the hELP LCST (FIG. 3*a*, right), the structures observed in conELP-Fb and hELP-Fb clots were consistent with the expected phase separation. Punctate spots of high ELP density indicated the formation of ELP-rich coacervates at T>LCST. The density of ELP-rich coacervates was greater in f-hELP-Fb clots than in f-conELP-Fb clots due to conELPs lacking the Q and K residues required for covalent integration. F-hELP coacervates were not randomly distributed relative to the Fb network, exhibiting some colocalization with Fb fibrils. Image analysis of hELP-Fb clots at 37° C. yielded a PCC value of 0.163±0.04. For f-conELP-Fb clots formed at 37° C., the inventors measured a PCC value of −0.04±0.06, indicating no spatial correlation. The average radii of hELP coacervates was determined from threshold images of three separate clots, and was found to be 0.57±0.17 μm (FIG. 7). The unimodal distribution of hELP coacervate sizes with a clear central peak suggests an energy balance that caps the growth of hELP coacervates inside Fb gels. Prior work on enzymatically cross-linked ELP hydrogels, or enzymatic integration of ELPs into collagen networks has reported that enzyme-mediated cross-linking was not inhibited above the LCST. The inventors' results are also consistent with these findings, and indicate that coacervation did not inhibit hELP association with Fb networks. In fact multivalent hELP-rich coacervates with locally increased concentration Q- and K-blocks may enhance FXIIIa-mediated cross-linking.

Example 3: Quantification of Pore Sizes

Pore size is an important architectural feature that contributes to Fb clot stiffness and resistance to enzymatic degradation. Covalent cross-linking of Fb fibrils by FXIIIa reduces pore size, while supplemental FXIIIa in vitro increases stiffness and resistance to fibrinolysis. The inventors investigated the effect of hELPs using a gravimetric perfusion assay where the inventors measured liquid flow rates through hELP-Fb clots and then used Darcy's law and a model developed by Carr and Hardin (L. W. Chan et al.,

*Sci. Transl. Med.* 2015, 7, 277ra29; M. E. Carr et al., *Am. J. Physiol.* 1987, 253, H1069) to estimate pore size.

Figure 8:
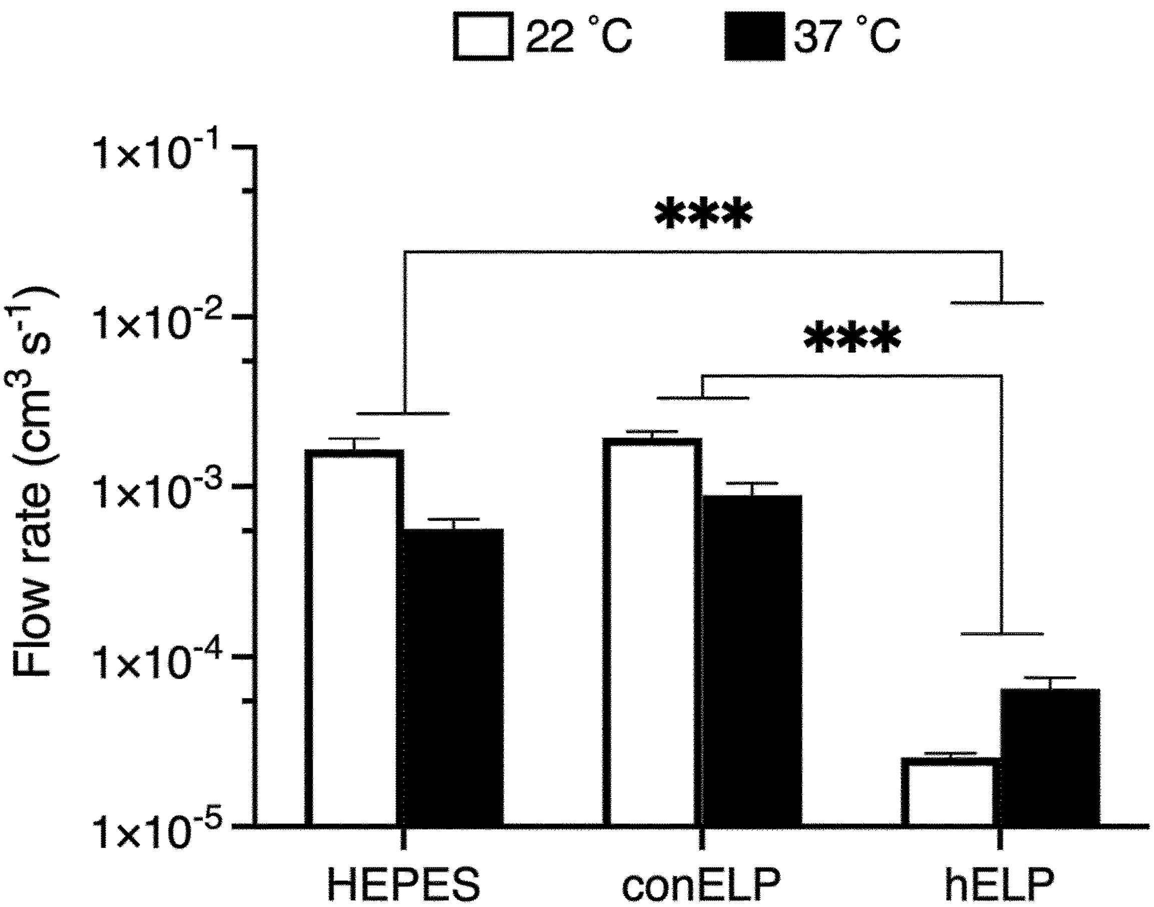
FIG. 8 shows differences in the volumetric flow rate of isotonic HEPES buffer through Fb clots containing HEPES buffer, 30 μM conELP, or 30 μM hELP at 22 or 37° C. Statistical significance was determined by means of a one-way analysis of variance (ANOVA) with Tukey's Post Hoc test. ***P<0.001.

At 22° C., the flow rates through HEPES-Fb and conELP-Fb control clots were ~100× higher than the flow rates through hELP-Fb clots (FIG. 8). These flow rates translated into average pore radii of 686.6±39.3, 761.2±41.8, and 73.6±5.4 nm for HEPES-Fb, conELP-Fb, and hELP-Fb clots, respectively (FIG. 3C). The ~10-fold smaller pore radius observed for hELP-Fb clots represented a significantly larger pore size reduction than previously reported for clots treated with either supplementary FXIII (a 2.1× reduction), or synthetic fibrin-binding polymers (a 1.5× reduction). SEM analysis of HEPES-Fb and hELP-Fb under vacuum was also qualitatively consistent with pore size reduction.

At 37° C., pore radii in both HEPES-Fb and conELP-Fb control clots were smaller than at 22° C. (390.3±28.9 nm and 504.3±51.3 nm, respectively), which the inventors attributed to a temperature-dependence of FXIIIa activity. In hELP-Fb clots however, the pore radius at 37° C. was 124.8±11.5 nm, slightly larger but not significantly different from the radius at 22° C. (FIG. 3*c*). An increase in temperature from 22° C. to 37° C. therefore did not lead to a significant change in apparent pore size as measured by gravimetric perfusion for hELP-Fb clots, as was observed in the controls. This could indicate that hELP-Fb clots are already maximally cross-linked at 22° C.

Example 4: Gelation Kinetics

Figure 4:
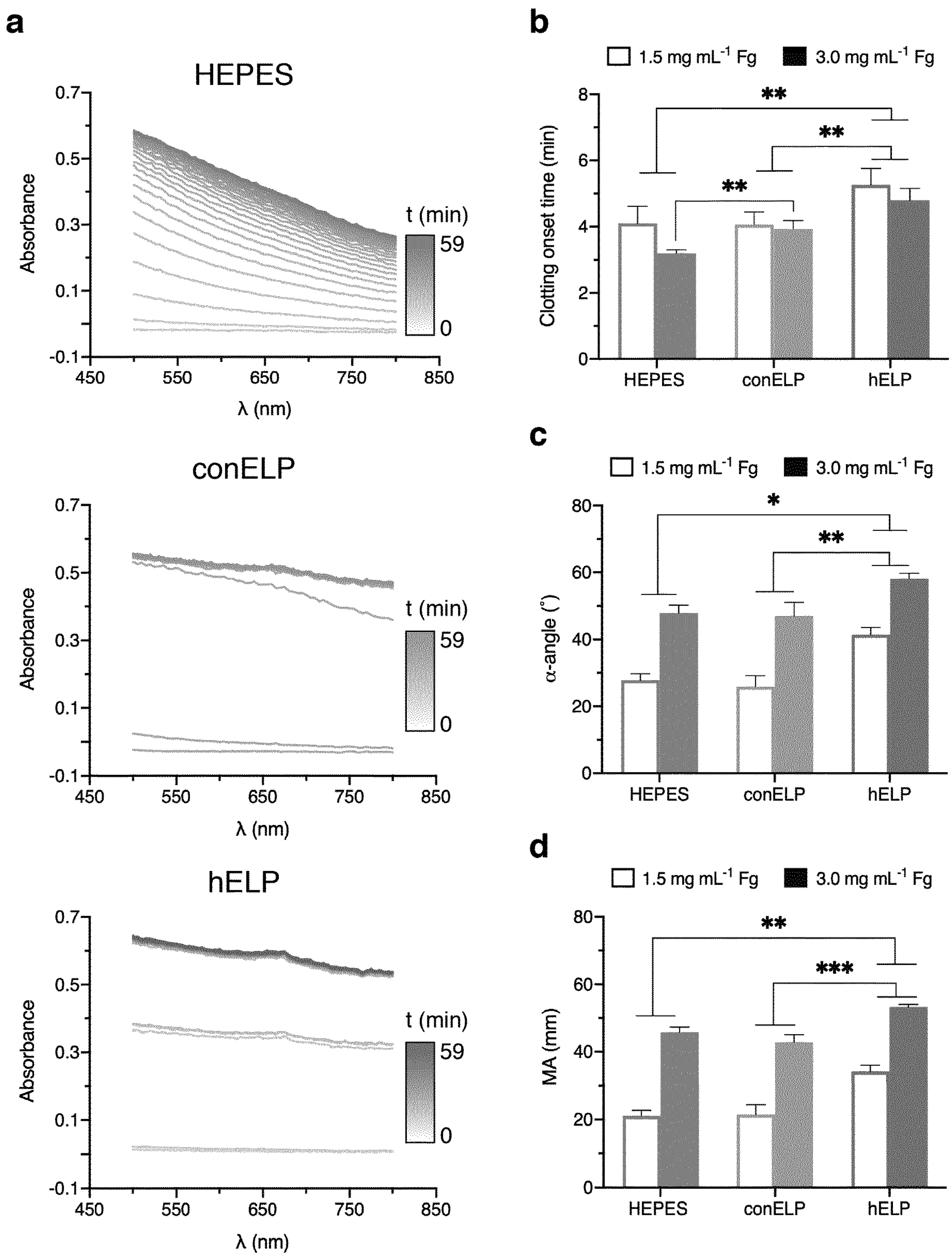
FIG. 4 shows gelation kinetics of Fb clots in the presence of hELP or conELP. a) Absorbance of gelling 2.2 mg $mL^{-1}$ Fb clots containing 30 μM hELP, conELP, or HEPES buffer at 37° C., across a range of wavelengths from 500-800 nm. Measurements were taken at 1-minute intervals over a period of 1 hour. b) Clotting onset time (R), c) α-angle and, d) maximum amplitude (MA) of Fb clots containing 30 μM hELP, conELP, or HEPES buffer as measured by thromboelastography at 37° C. Data in panels b, c, and d are shown as mean±SD (n=3) *P<0.05, P<0.01, *P<0.001; one-way ANOVA with Tukey's post hoc test.

The inventors investigated the effect of hELPs on gelation kinetics using a turbidity assay (L. W. Chan et al., *Sci. Transl. Med.* 2015, 7, 277ra29; A. S. Wolberg, *Blood Rev.* 2007, 21, 131; E. Mihalko, A. C. Brown, *Semin. Thromb. Hemost.* 2019) in a UV-Vis spectrophotometer (FIG. 4*a*). Absorbance values of gelling Fb clots were measured from 500-800 nm over a period of 1 hr at 37° C. Several distinct gelation profiles emerged across the different groups. HEPES-Fb buffer control clots showed a steadily increasing absorbance at all wavelengths over the time course of the experiment. ConELP-Fb clots reached a maximum absorbance after 5 minutes of gelation, after which the absorbance remained constant. HELP-Fb clots showed a two-phase gelation profile, wherein the absorbance rapidly rose within the first 3 minutes, and then increased more slowly to a final maximum at 8 minutes. Analysis of the turbidity of Fb clots as a function of wavelength was previously used to estimate the mass/length ratio of fibres, however, due to unknown refractive index differences and turbidity of hELP coacervates within the hELP-Fb composite hydrogels, such an analysis would not be straightforward for this system.

Figure 9:
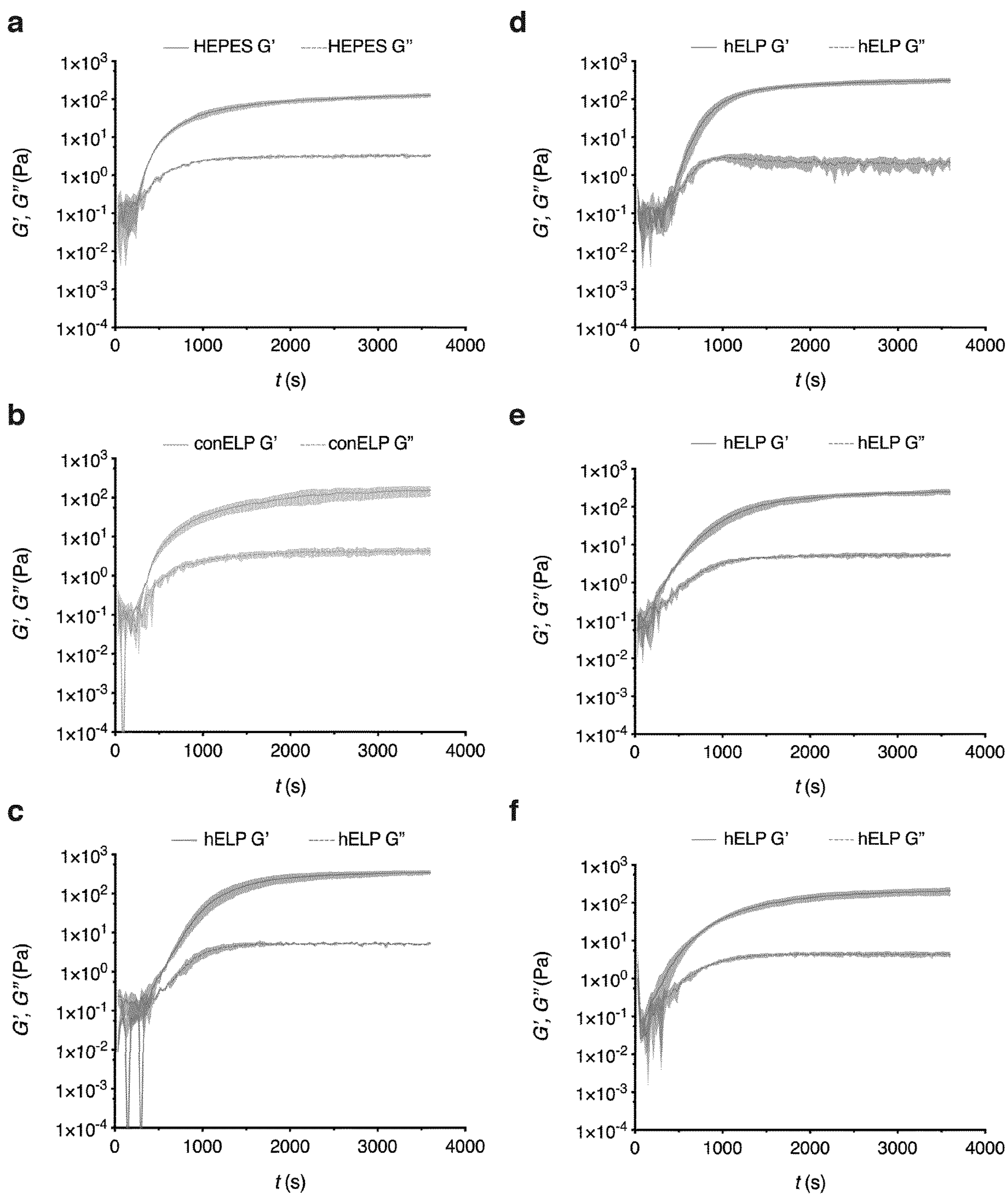
FIG. 9 shows evolving storage (G') and loss moduli (G") of 2.2 mg mL-1 Fb clots containing a) HEPES, b) 30 μM conELP, c) 30 μM hELP, d) 20 μM hELP, e) 10 μM hELP, and f) 5 μM hELP as measured over 1 h gelation time at 37° C. Clots were subjected to a constant oscillatory shear stress (γ=0.1%; f=1 Hz). Shaded areas show one standard deviation from the mean (n=3).
Figure 10:
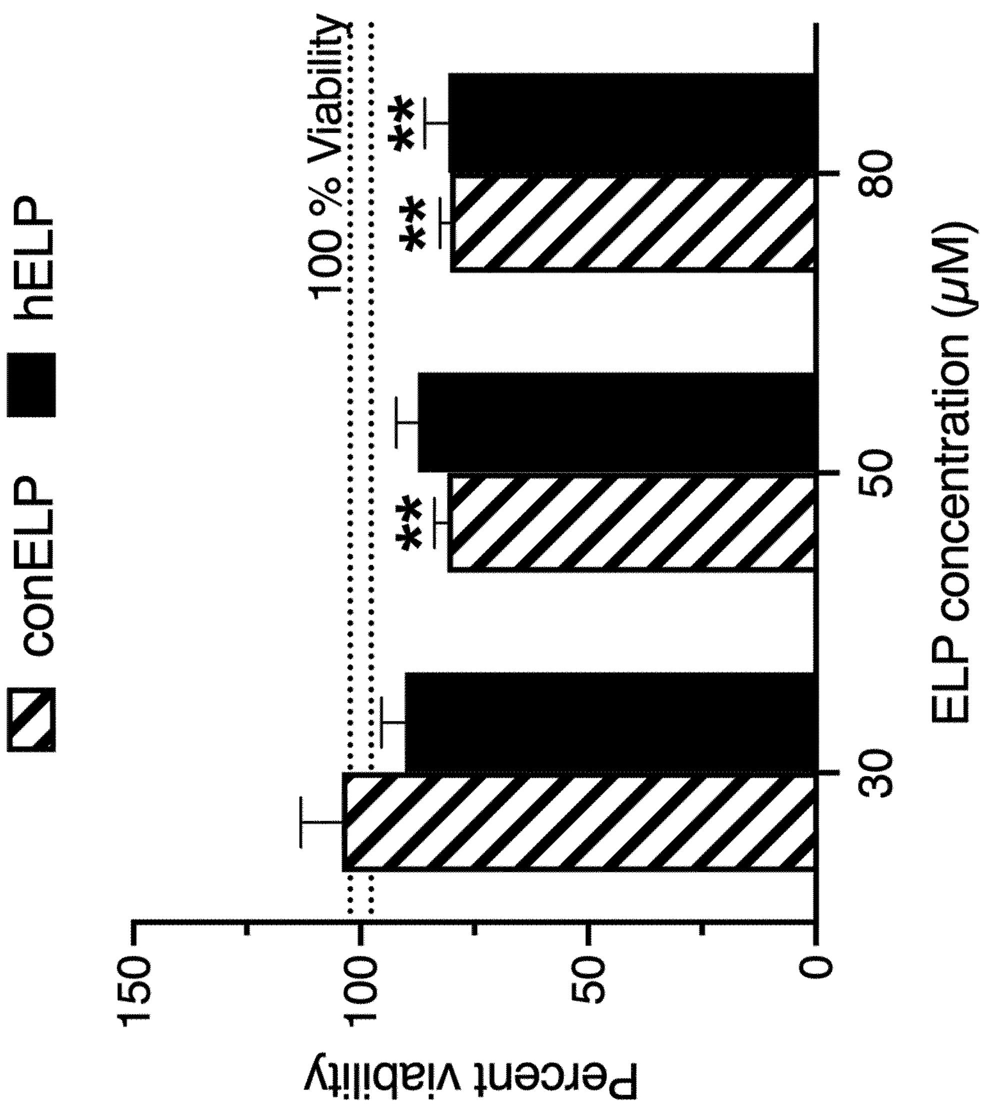
FIG. 10 shows cell viability of human dermal fibroblasts (neonatal; HDFn) following 24 h exposure to various concentrations of purified hELP and conELP under physiological conditions, as compared to a control containing only media. Data are shown as mean±SD (n=4) **P<0.01; one-way ANOVA with Tukey's post hoc test.
Figure 11:
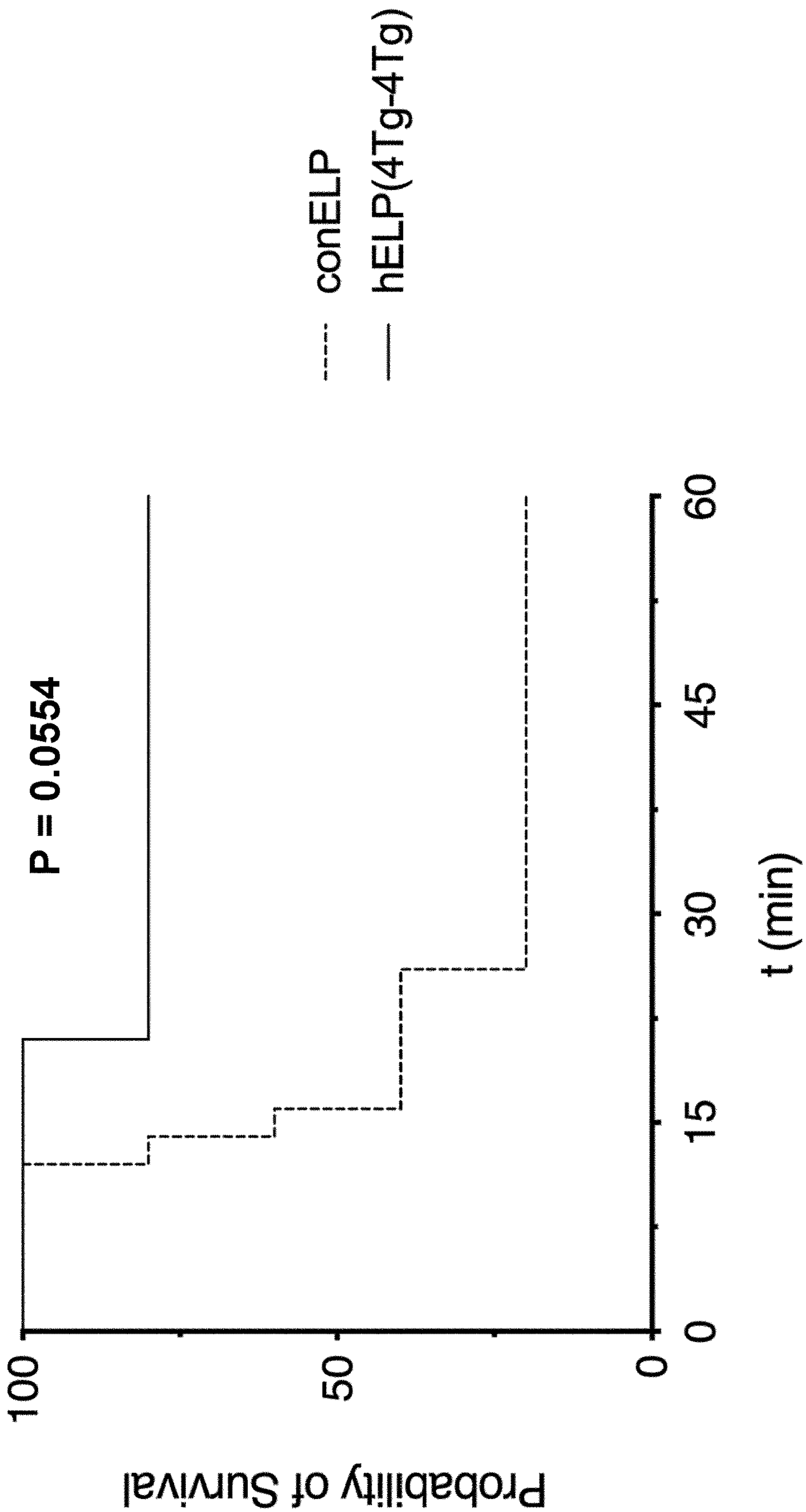
FIG. 11 shows the survival curves of rats in a femoral artery injury bleeding model following intravenous administration of approx. 140 mg kg-1 of hELP(4Tg-4Tg) or inactive conELP (see Example 10). The first 15 minutes of the experiment (following release of clamps surrounding the femoral artery injury) constituted the free bleed period, after which time fluid resuscitation was undertaken in order to maintain MAP above 60 mm Hg when possible. Animals were euthanized when MAP fell below 20 mm Hg. The hELP polymers were effective compared to conELP at a significance level of p=0.0554 (log-rank Mantel Cox test).

The inventors further measured gelation kinetics of hELP-Fb clots using low-strain oscillatory shear rheology under physiological conditions, focusing in particular on the shear storage (G') and loss (G") moduli. For HEPES-Fb and conELP-Fb clots, an initial lag phase was followed by a period of rapid gelation, and a secondary phase of slower asymptotic growth of G' (FIG. 9). The gelation time for conELP-Fb and HEPES-Fb clots (defined as the point where G'=G") occurred at ~270 s for both samples, while the gel point for hELP-Fb clots occurred significantly later at ~510 s. Following onset of gelation, G' of hELP-Fb clots increased more rapidly than in HEPES-Fb or conELP-Fb clots. The maxima of the first order derivatives were 0.15, 0.14, and 0.39 Pa $s^{-1}$ for HEPES-Fb, conELP-Fb clots, and hELP-Fb, respectively. The presence of hELP coacervates therefore had an inhibitory effect on time until initiation of clotting, but a positive effect on clot growth rate and maximum stiffness following initiation.

Example 5: Influence of hELPs in Thromboelastography

Thromboelastography (TEG) is a clinical technique for measuring the clotting capacity of blood (D. Whiting, J. A. DiNardo, *Am. J. Hematol.* 2014, 89, 228.). Here, the inventors evaluated three TEG parameters, namely R, which measures the time to initiation of clot formation, α-angle which measures clot formation rate, and maximum amplitude (MA) which measures clot stiffness. Here too, a similar picture emerged of two-phases of hELP-Fb clot formation as was observed in the turbidimetric and rheological experiments described above. The initiation of clotting required more time in hELP-Fb clots than in conELP-Fb or HEPES-Fb clots, at both low and high Fb concentrations (FIG. 4*b*). However, following the onset of clotting, hELP-Fb clots containing 1.5 mg $mL^{-1}$ Fb had a significantly higher α-angle (41.43±2.15°) than HEPES-Fb or conELP-Fb controls, (27.83±1.95°, 25.93±3.26° respectively) (FIG. 4C). When the Fb concentration was increased to 3.0 mg $mL^{-1}$, the increase in α-angle for hELP-Fb clots relative to controls was more modest. In this case, hELP-Fb clots had an α-angle of 58.2±1.6° while α-angles for HEPES-Fb and conELP-Fb clots were 47.9±2.31° and 47.07±4.04°, respectively. In previous studies, FXIII was found to be critical to the secondary phase of clot stiffening during gelation, and as hELPs are integrated into Fb clots by FXIII, it may be the case that their presence increases the rate of this secondary phase.

The effect of hELPs on MA values was similar to the one observed for R and α-angle. For hELP-Fb clots containing 30 μM hELP and 1.5 mg $mL^{-1}$ Fb, MA rose 62% and 59% relative to HEPES and conELP-containing clots, respectively. For hELP-Fb clots formed with 3.0 mg $mL^{-1}$ Fb, MA was 16% higher than HEPES-Fb clots, and 24.5% higher than conELP-Fb clots (FIG. 4*d*). Taken together, these TEG results were consistent with shear rheology, and indicated that hELPs had a more pronounced positive effect on clot properties for clots with lower, sub-critical threshold concentrations of Fg.

Example 6: Effect of hELP Coacervates on Fb Clot Mechanics

In clinical hemostasis, Fb concentrations below ~2.3 mg $mL^{-1}$ are associated with increased mortality. The inventors used oscillatory shear rheology to measure the effect of hELPs on clot stiffness (G') with Fb concentrations above and below this threshold. At 22° C., no significant differences in G' were observed at any Fb concentration for HEPES-Fb, conELP-Fb or hELP-Fb clots (FIG. 5*a*). At 37° C., however, the inventors found a significant increase in G' across all Fb concentrations for hELP-Fb clots. HELP-Fb clots with the lowest Fb concentration (1.5 mg $mL^{-1}$) exhibited G' of 201.3±16.4 Pa, which was significantly higher than those of conELP-Fb (71.0±11.6 Pa) or HEPES-Fb (45.0±12.8 Pa) clots. The G' of hELP-Fb clots formed with 1.5 mg $mL^{-1}$ Fb was equivalent to the G' of control clots formed at a physiological Fb concentration of 2.2 mg $mL^{-1}$. This indicated that at T>LCST, hELP coacervates restored clot stiffness to physiological values under simulated conditions of TIC and depleted Fg.

Example 7: Influence of hELPs on Strain-Stiffening of Fb Clots

Strain-stiffening in Fb clots has been attributed to the multi-scale structural organization of Fb networks, from single monomers, to protofibrils, to protofibril bundles, and fibres. According to this theory, as Fb networks are strained, force is first entropically dissipated by minimizing thermal fluctuations of flexible inter-fibril cross-links, and subsequently through the stretching of fibrils themselves. Eventually, at higher tension the secondary, tertiary, and quaternary structural elements of folded regions within Fb domains are denatured, giving rise to strain stiffening behaviour that is uncommon in synthetic cross-linked polymer networks (I. K. Piechocka et al., *Biophys. J.* 2010, 98, 2281; I. K. Piechocka et al., *Soft Matter* 2016, 12, 2145).

To determine what effect hELPs have on Fb strain-stiffening, the inventors performed oscillatory rheology using strain ramps from 0.1-100% (FIG. 5*b*). At low strains (0.1-1%), hELP-Fb clots containing 30 μM hELP and 2.2 mg $mL^{-1}$ Fb exhibited an increase in G' as compared to conELP-Fb or HEPES-Fb clots, consistent with observations in the low amplitude frequency sweep experiments (FIG. 5*a*). At medium (1-10%) and high strains (10-100%), all clots showed strain-stiffening behaviour, however, the onset strain of the stiffening was higher for hELP-Fb (~10%) than for conELP-Fb or HEPES-Fb clots (~2-3%). The rate of strain stiffening was higher in HEPES-Fb and conELP-Fb clots than for hELP-Fb clots, as indicated by the maxima of the first derivative for each curve (38.1, 38.8, and 23.1 Pa, respectively). At 100% strain, G' for all clots was roughly equal (~1400-1500 Pa). Comparing G' between 0.1 and 100% strain, hELP-Fb clots stiffened 4.6-fold, while conELP-Fb and HEPES-Fb clots stiffened 8.8 and 8.4-fold, respectively. Considering these results in the context of Fb hierarchical structure, it seems likely that by cross-linking protofibrils, hELPs minimize thermal fluctuations of unstructured regions of the network in the low strain range. Once the clot is sufficiently stretched, the elastic response is dominated by stretching of individual protofibrils, and therefore the addition of additional cross-links in the form of hELP coacervates no longer plays a role. Previous studies have shown that supplemental FXIII increases the elastic modulus of Fb clots at low strains within the linear viscoelastic region for fibrin, but not in the non-linear portion of the stress-strain curve, similar to what the inventors observed here with addition of hELPs.

The phase-transition-dependence of the stiffening effect of hELPs in Fb clots can be explained in several ways. Firstly, the high local concentration of hELP molecules in the coacervate may promote the formation of more intermolecular hELP-hELP cross-links, establishing a secondary network that is stiffer than Fb in the low strain range. In vivo, a similar effect is observed in the phase-separation driven formation of biomolecular condensates, wherein local concentration enhancement of substrates and enzymes can accelerate chemical reactions. This has been shown to increase rates of reaction in actin polymerization and RNA catalysis, for example. Secondly, aggregation of hELPs above their LCST may drive the formation of a secondary network of cross-links between Fb molecules, independent of the formation of inter-hELP cross-links. The formation of secondary networks in hydrogels by thermal assembly of ELPs was also reported by Wang et al., who showed that the aggregation of hydrazide-modified ELPs cross-linked into Hyaluronic Acid hydrogels resulted in a mechanical stiffening of those materials. Finally, the phase separation of hELPs bound to Fb may exert mechanical forces on Fb fibres, creating a strain-stiffening effect even in the absence of external tension, recapitulating the active cell-driven contractile strain-stiffening that occurs in fibrin networks having imbedded fibroblasts and platelets. Strain-stiffening is a well-known property of Fb networks and ELP coacervation is known to stiffen ELP hydrogels and exert mechanical forces. There is evidence that the mechanical force of molecular aggregation is applied in other contexts in vivo: Shin et al. recently showed that the phase-separation of IDPs associated with chromatin functions to physically pull-together distal genomic elements, while mechanically excluding others, in a mechanism that controls DNA transcription (Y. Shin et al., *Cell* 2018, 175, 1481.). However, given than the stiffening effect is observed for hELPs that are pre-heated/aggregated prior to Fb polymerization, active contraction/stiffening of the network by hELP coacervates seems unlikely.

Example 8: Effect of hELP Coacervates on Plasminolysis

In the body, clots are enzymatically degraded by the protease plasmin, which is generated from plasminogen upon activation by tissue-plasminogen activator (tPa). The proteolytic activity of plasmin is regulated spatio-temporally by binding of tPa and plasminogen to exposed cryptic binding sites on Fb clots. It has previously been shown that cross-linking by FXIIIa has an inhibitory effect on fibrinolysis in vivo. Since hELP coacervates are covalently integrated into Fb clots by FXIIIa, the inventors hypothesized that hELPs could extend the lifetime of Fb clots in the presence of plasmin. To evaluate this, the inventors performed time-lapse confocal microscopy.

Figure 6:
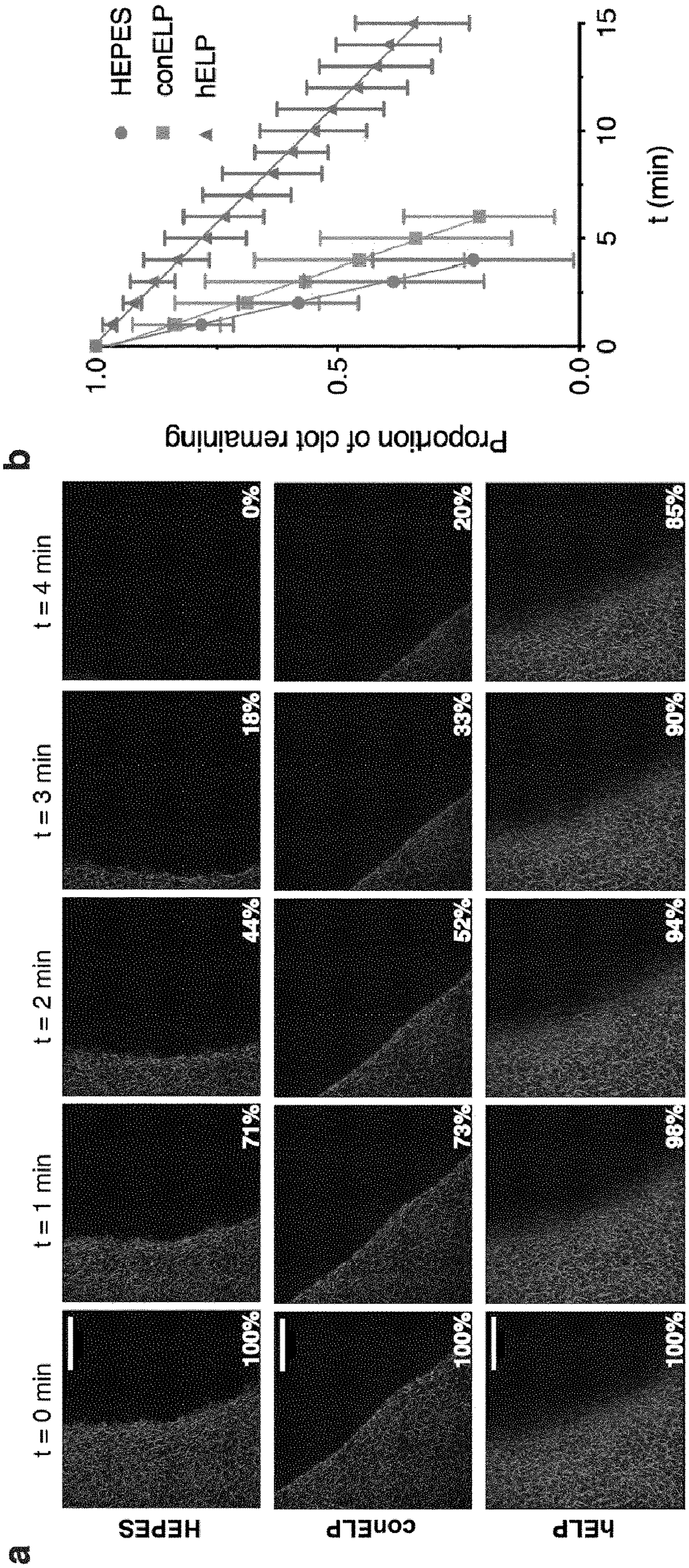
FIG. 6 shows degradation of Fb clots by plasmin. a) Time-lapse Confocal images of 1.5 mg $mL^{-1}$ Fb clots containing 30 μM hELP, conELP, or HEPES buffer, following exposure of the clot front to 10 μg $mL^{-1}$ plasmin at 37° C. Scale bars are 60 μm. b) Quantification of the proportion of clot lysed over time for 1.5 mg $mL^{-1}$ Fb clots containing 30 μM hELP, conELP, or HEPES buffer, as determined from confocal images of multiple clots (n=3).

Fluorescent Fb clots containing 30 μM hELP, conELP, or an equivalent volume of HEPES were formed in a chambered coverslip, and a solution of plasmin at physiological concentration was applied to the clot front. Images were taken at regular time intervals and analysed in order to assess the proportion of clot lysed over time. Results indicated large differences in plasminolysis rates between hELP and control clots. Typically, HEPES control clots were completely degraded from the microscope field of view 4 minutes after the application of plasmin, whereas roughly 20% of conELP-Fb and 85% of hELP-Fb clot remained (FIG. 6). The lysis rate in hELP-Fb clots was roughly three times slower than that found in conELP-Fb clots, and roughly five times slower than that found in HEPES-Fb clots. HELPs do not contain sequences recognized by plasmin, therefore the additional non-degradable component in the gel inhibited fibrinolysis.

Example 9: Cytotoxicity of hELPs

ELPs are generally accepted as biocompatible and non-toxic, however, as with many recombinantly produced proteins from *E. Coli* there is the potential for the retention of bacterial endotoxins (i.e. lipopolysaccharides, LPS) in the purified protein product, which can lead to inflammatory and immune responses in the body. Here, the inventors applied an in vitro resazurin-based cytoxicity assay on neonatal human dermal fibroblasts (HDFn) to measure cytotoxicity of hELPs. For this experiment, ELPs were subjected to additional dialysis and lypholization steps following ITC purification to remove low molecular weight and non-aggregated LPS. No significant reduction in cell viability was observed following 24 h exposure of HDFn cells to hELP and conELP at the standard working concentration of 30 μM, as compared to untreated control cells (FIG. 6). There was a significant reduction in HDFn viability observed when cells were exposed to 50 μM conELP, while exposure to 80 μM ELP led to a significant reduction in cell viability for both hELP and conELP treatments. However, even at the highest tested concentration of 80 μM, cell viability did not fall below 80% of the control. hELP and conELP therefore have minimal cytotoxic effects under these conditions.

Example 10: In Vivo Test of Procoagulant hELPs

The efficacy of hELPs as hemostatic agents was evaluated using a rat in vivo model of bleeding. Ten male CD rats were divided into 2 study groups: hELP(4Tg-4Tg; SEQ ID NO 16), conELPs (control ELPs). 4Tg refers to the 'Q-block' transglutaminase substrate sequence recognized by coagulation FXIIIa (SEQ ID NO 003). The control ELPs were modified such that the glutamine in the Q-block sequences had been mutated to glycine, and so they cannot be recognized by FXIII. On the day of surgery, rats were anesthetized using isoflurane, placed on warming beds, and had two catheters inserted: one in the carotid artery, and another in the jugular vein. Once baseline levels of $CO_2$, $O_2$, and lactate were established, clamps were placed on proximal and distal ends of the left femoral artery, after which a 3 mm incision was made in that artery. A controlled catheter bleed was conducted to lower each animal's mean arterial pressure (MAP) to 40-60 mm Hg, after which point the clamps on the femoral artery were removed, and the rats were given a bolus injection (up to 2 mL min-1) of the indicated treatment at a volume of 5 mL kg-1. The targeted final concentration of ELP in the blood was 30 μM, assuming a blood volume of 64 mL kg-1 for each rat. This translated to a dose of approx. 140 mg of ELP/kg of body weight. Following clamp removal, animals were allowed to bleed freely for 15 minutes, while blood loss volumes were measured using preweighed gauze. After the 15-minute free-bleed period, a blood sample was taken for measurement of blood gases, as well as prothrombin time. Saline was then administered to animals as needed, in order to raise MAP above 60 mm Hg (at a rate of 3 mL/kg/min, and up to a total volume of 60 mL kg-1). Blood loss volume and MAP were continuously monitored until MAP fell below 20 mm Hg, or until the end point of the experiment (t=75 m), at which time animals were euthanized. This study design was approved by the Institutional Animal Care and Use Committee at Charles River Laboratories.

Methods

Unless otherwise stated, all chemicals were purchased from Sigma-Aldrich (Buchs, Switzerland). Plasmids with genes encoding for ELP($A_2V_8E_1$), ELP($A_2V_8E_1$)-Tgf11, ELP($A_2V_8E_1$)-GSKGS (the GSKGS module is SEQ ID NO 11), ELP($A_2V_8E_1$)-Tgf11(Q65G), and ELP($A_2V_8E_1$)-GSGGS (the GSGGS module is SEQ ID NO 15) were synthesized by GeneArt (Thermo Scientific). Human fibrinogen (FIB 3, plasminogen, fibronectin and von Willebrand Factor depleted), thrombin, and FXIIIa were purchased from Enzyme Research Laboratories (Rheinfelden, Switzerland). Fluorescently tagged fibrinogen (Fg-488) was purchased from Thermo Scientific (Basel, Switzerland).

Method 1: ELP Expression & Purification hELP and conELP proteins were designed and produced using standard molecular cloning techniques. Genes encoding the full length ELPs were produced starting from one of five 11-pentapeptide gene monomers: A2V8E1-Tgf11, A2V8E1, A2V8E1-GSKGS (the GSKGS module is SEQ ID NO: 11), A2V8E1-Tgf11(Q65G), or A2V8E1-GSGGS (the GSGGS module is SEQ ID NO: 15). These were iteratively digested and ligated together according to a previously described technique for the elongation of repetitive gene sequences, known as Recursive Directional Ligation. Once a gene encoding an ELP of the desired length and composition was prepared, it was inserted into a pet28a expression vector, and the resulting plasmid was transformed into BL21 (DE3) *E. coli*. ELPs were expressed for 24 h at 37° C. in 1 L of Terrific Broth (TB) without the addition of inducers, relying instead on the leakiness of the T7 promoter. Following expression, the cell pellet was centrifuged, re-suspended in 40 mL 20/150 mM HEPES/NaCl, and lysed by 3 cycles of ultrasonic disruption. The lysate was centrifuged at 4° C. to remove cellular debris, and the ELPs were subsequently purified by Iterative Transition Cycling (ITC). Briefly, 1 M NaCl was added to the supernatant remaining after centrifugation of the cell lysate. The sample was heated to 65° C. for 10 minutes, and centrifuged at 18 000 g at 40° C. for 15 min. The supernatant was discarded, and the resulting pellet was resuspended in 6 mL of cold HEPES buffer. The resuspended pellet was centrifuged again at 18 000 g at 4° C. for 15 min, and any contaminants that could not be resolubilized in cold buffer were discarded. Together these steps constituted one round of ITC, and the process was repeated two more times to yield the final ELP solutions, which were aliquoted and stored as-is at −20° C. prior to use. Typical yields for a single expression ranged from 50-100 mg/L of culture.

Method 2: Characterization of ELP Cloud Points

The cloud points of hELPs and conELPs were measured at 30 μM concentration. ELPs were dissolved in 20/150 mM HEPES/NaCl buffer (w/20 mM $CaCl_2$) to the appropriate concentration, transferred to cuvettes, and placed into a UV-Vis spectrophotometer (Evolution 260 Bio, Thermo Scientific) at 15° C. Samples were allowed to equilibrate to the starting temperature for 10 minutes, after which a temperature ramp was performed from 15-60° C. at a rate of 1° C. $min^{-1}$. Absorbance at 350 nm was measured every 0.25 min, and a blank reading from a cuvette containing only HEPES was subtracted from this value to yield the corrected absorbance value; this was then converted to transmittance and normalized to maximum and minimum absorbance values. The cloud point for each ELP was defined as the point where the normalized transmittance fell below 95%.

Method 3: In Vitro Crosslinking of ELPs by FXIIIa

The ability of hELPs or conELPs to be crosslinked by FXIII was assessed by SDS-PAGE. hELPs or conELPs were diluted to a concentration of 50 μM in HEPES buffer; 0.2 U $mL^{-1}$ Thrombin, and 20 mM $CaCl_2$ were also added to each sample in order to replicate the standard clotting conditions used throughout this work. FXIIIa was added to experimental samples at a final concentration of 10 μg $mL^{-1}$, while control samples received an equal volume of HEPES buffer. All samples were then incubated at 37° C. for 1 hr, and subsequently run on a non-reducing SDS-PAGE. Samples were stained using a Coomassie-based Instant Blue stain, and imaged using a ChemiDoc Mp imaging system (Bio-Rad).

Method 4: Rheological Measurements of ELP-Containing Fb Clots

The mechanical properties of in vitro Fb clots containing hELP, conELP, or an equal volume of HEPES buffer were assessed using an Anton Paar MCR 302 Rheometer with a cone-plate geometry (d=25 mm; 1° angle). To determine their oscillatory shear moduli, frequency sweep measurements where performed, whereby clotting solutions were prepared containing 1.5, 2.2, or 3.0 mg $mL^{-1}$ fibrinogen (Fg), 30 μM hELP or conELP, or HEPES buffer, 20 mM $CaCl_2$, and 0.2 U $mL^{-1}$ Thrombin. Immediately upon the addition of Thrombin, 90 μL of the clot solution was transferred to the preheated Peltier plate of the rheometer at 37° C., the measuring cone was lowered onto the sample, and the cone was spun at 60 rpm for 5 seconds to ensure proper mixing and sample distribution. Silicone oil (η=100 cSt) was applied to the edges of the sample in order to prevent evaporation, and the clot was allowed to equilibrate for 1 hr, after which time a frequency sweep was performed from 0.1-3 Hz (γ=1%; previously determined to be within the Linear Viscoelastic Region (LVE) for this material).

To assess the effects of temperature on the stiffness-modulating properties of ELPs in Fb clots, samples containing 1.5 or 3.0 mg $mL^{-1}$ Fg, hELP, conELP, or HEPES buffer were formed as before on the Peltier plate of the rheometer preheated to either 22 or 37° C. Following equilibration of the clots, a frequency sweep was performed as described above.

To assess the effects of ELPs on the strain-stiffening behaviour of Fb clots, samples containing 2.2 mg $mL^{-1}$ Fg, and 30 μM hELP, conELP, or HEPES buffer were formed as before at 37° C. between the cone and plate of the rheometer. Following equilibration for 1 hr, an oscillatory strain sweep was performed from 0.1-100% strain (f=1 Hz).

To follow the gelation kinetics of Fb clots formed in the presence of ELPs, clotting solutions were prepared as described above, and then placed between the cone and plate of the rheometer, which had been preheated to 37° C. A small amplitude oscillatory shear stress was applied to the forming clot ((γ=1%; f=1 Hz) and the evolution of G' and G" were measured. The gel point for each clot was defined as the point where G' exceeded G" and did not subsequently fall below G" for the remainder of the experiment.

Method 5: Turbidimetry Measurements of Gelation Kinetics

The evolution of turbidity in gelling Fb clots was measured over a range of wavelengths in order to study gelation kinetics. In a typical experiment, clotting solutions consisting of 2.2 mg $mL^{-1}$ Fg, 20 mM $CaCl_2$, 0.1 U $mL^{-1}$ thrombin, and one of 30 μM hELP, 30 μM conELP, or HEPES, were prepared in cuvettes and immediately transferred to an Evolution 260 Bio UV-Vis spectrophotometer (Thermo Scientific) that had been preheated to 37° C. Absorbance was then measured across the range of 500-800 nm at intervals of 5 nm, and this scan was repeated every minute for the 1 hour time course of the experiment.

Method 6: Perfusion Assay for Determining Fb Clot Pore Size

The pore sizes of Fb clots with or without ELPs were evaluated via a perfusion assay which had been adapted from a previous work by Carr and Hardin (Shin et al., Cell 2018, 175, 1481). Clots were formed at the bottom of upright gravity filtration columns which had had their tips cut off and sealed by parafilm, in order to support the clotting solution during gelation. 1 mL of clotting solution was used in each experiment, consisting of 1.5 mg $mL^{-1}$, 20 mM $CaCl_2$, 0.1 U $mL^{-1}$ Thrombin, and 30 μM hELP or conELP, or an equal volume of HEPES buffer. Clots were allowed to form for 1 hr at 22 or 37° C., after which time 13 mL of isotonic and isothermal HEPES buffer was dispensed on top of each clot, and the clots were allowed to equilibrate for 10 minutes. The flow rate was then determined gravimetrically, by measuring the mass of buffer passing through the clots every 10 minutes for 50 minutes. The pore radii ($r_p$) of clots with and without ELPs were then calculated from the volumetric flow rate according to Darcy's Law, and a model developed by Carr and Hardin for determining the pore sizes of Fb clots containing embedded erythrocytes (Shin et al., Cell 2018, 175, 1481):

$$Da = \frac{V\eta h}{AtP}$$

$$r_p = \frac{0.5093}{Da^{-1/2}}$$

Where V is the volumetric flow rate, η is the viscosity of water (0.9544 mPa s@22° C., 0.6913 mPa s@37° C.), h is the length of the clot, A is the cross-sectional surface area, t is time, and P is the average hydrostatic pressure exerted by buffer above the clot over the course of the experiment.

Method 7: Confocal Imaging

Confocal microscopy was used to study the integration of hELPs into Fb networks, as well as Fb network degradation in the presence of plasmin. Fluorescent hELP (f-hELP) or conELP (f-conELP) was prepared by preferentially functionalizing these proteins at N-terminal amines with Atto-647-NHS dye. In a typical reaction, Atto-647-NHS was dissolved in DMSO, and added to a solution of hELP or conELP at a ratio of 1.2 dye molecules per 1 ELP molecule. The reaction was performed at pH 8.0, in order to preferentially target N-terminal amines, which have a lower pka than the ε-amino group of lysine (approx. 8 and 10, respectively). The reaction was allowed to proceed for 1 hr at room temperature, and then the reaction was quenched by the addition of 100× excess of TRIS-HCl. The functionalized ELP was then purified from the reaction mixture by two rounds of ITC, as described above.

For simple imaging experiments clots were formed in the channels of an Ibidi μ-slide VI 0.5 (Glass Bottom) from 40 μL clotting solutions consisting of 1.5 mg $mL^{-1}$ fibrinogen (spiked with 1% fluorescent Fg-488), 0.2 U $mL^{-1}$ thrombin, 20 mM $CaCl_2$, and one of 30 μM f-hELP, 30 μM f-conELP, or HEPES buffer. Clots were formed for 1 hr at either 22 or 37° C., and then transferred to the imaging chamber of A Nikon Ti2-A1 confocal microscope which had been preheated to the applicable temperature. 40 μL of buffer were added to each port of the slide in order to avoid loss of water from the clot over the course of the experiment. 5.06 μm, 5-slice z-stacks were then taken at three different positions in each clot using first 488 (Fb channel) and then subsequently 640 nm (ELP channel) lasers. Three different clots were imaged per treatment group.

For degradation experiments, clots were formed in μ-slide ibidi 8-well chambered coverslips from 100 μL of clotting solution consisting of 1.5 mg $mL^{-1}$ fibrinogen (spiked with 1% Fg-488), 0.2 U $mL^{-1}$ thrombin, 20 mM $CaCl_2$, and one of 30 μM hELP, 30 μM conELP, or HEPES buffer. Samples were allowed to gel for 1 hr at 37° C., after which half of each formed clot was cut out of the wells of the coverslip with a scalpel. The cover slips were then placed into the imaging chamber of the microscope at 37° C., and the edge of the Fb network was located using the 488 nm laser. A preheated solution of 10 μg $mL^{-1}$ plasmin was then applied to the edge of the clot, and images were taken every 10 s until the clot had been completely removed from the microscope field-of-view. Images were taken at three different position in each clot, and three different clots were made for each treatment group.

Method 8: In Vitro Cell Viability Assay

The effects of ELP coacervates on the viability of human dermal fibroblasts (neonatal; HDFn) cells were investigated by means of a resazurin-based assay. HDFn cells were seeded into the wells of a 96-well tissue culture treated plate at a density of 20 000 cells/well and were incubated for 24 h at 37° C., 5% $CO_2$. Cells were then treated with stock solutions of conELP or hELP dissolved in DMEM, to final concentrations of 30, 50, or 80 μM ELP. Cells in control wells were treated with an equivalent volume of DMEM, and then the plate was incubated for an additional 24 h at 37° C., 5% $CO_2$. A stock solution of resazurin in 10 mM PBS was then applied to each experimental and control well, up to a final concentration of 10 μg $mL^{-1}$, the plate was incubated at 37° C. for 4 h, and then the fluorescence of each well was measured on a Safire II plate reader ($\lambda_{exc}$=531 nm, $\lambda_{emi}$=572 nm). The final cell viability for each treatment was determined by taking the average fluorescence intensity per treatment (minus a cell-free blank) and dividing it by the average fluorescence intensity of the ELP-free control.

Method 9: Fluorescent Labelling of hELPs

To study FXIIIa-mediated integration of hELPs into Fb clots, the inventors labelled hELPs and conELPs preferentially at the N-termini of the proteins with the fluorescent dye Atto647-N-hydroxysuccinimide (Atto647-NHS). By performing the reaction at pH 8, the inventors selectively targeted α-amino groups with lower $pK_a$, preserving lysine ε-amino groups in the K-block for FXIIIa-mediated cross-linking post labelling. Using the extinction coefficients for hELP/conELP ($\varepsilon_{280}$=2.75×$10^4$ $M^{-1}$ $cm^{-1}$) and Atto647 ($\varepsilon_{647}$=1.5×$10^5$ $M^{-1}$ $cm^{-1}$), the inventors determined the average number of fluorescent dye molecules per ELP molecule to be ~0.95. The inventors tested whether fluorescent-hELPs (f-hELPs) maintained the ability to be cross-linked by FXIIIa using SDS-PAGE. Disappearance of the single f-hELP band at ~69.5 kDa in samples containing FXIIIa indicated that sufficient active lysine residues remained following fluorescent labelling with Atto647-NHS to allow f-hELPs to be cross-linked by FXIIIa.

Sequence

Elastin-like polypeptides (ELPs) are intrinsically disordered protein-based polymers derived from the hydrophobic domain of the human extracellular matrix protein tropoelastin, comprising repetitive pentapeptide VPGXG sequences (SEQ ID NO: 12), where X can be any amino acid excluding proline. VPGXG (SEQ ID NO: 12) represents the essential portion of the endogenous sequence of human tropoelastin that was used in this invention.

The inventors designed hemostatic ELPS (hELPs) to have an ABC triblock architecture. A repetitive ELP component was present in all three blocks and comprised 11 VPGXG (SEQ ID NO 012) pentapeptides with alanine, valine, and glutamic acid residues in guest residue positions at a ratio of 2:8:1 ($A_2V_8E_1$). While the residues at the guest position could in theory be altered from this composition, the current design was chosen in order to produce hELPs that had a transition temperature in the range of physiological temperature. The N-terminal hELP block additionally contained 4 transglutaminase tags (referred to as the Q-block), which comprised a glutamine residue embedded within a contextual peptide sequence (DQMMLPWPAVAL (SEQ ID NO 003)) previously shown to be recognized with high-specificity by human FXIIIa. Through the inclusion of these sequences in the broader hELP sequence, the inventors designed hELPs to be selectively integrated into Fb networks at wound sites in the body where FXIII is activated, while avoiding off-target interactions with circulating fibrinogen. The middle hELP block was the phase separation block consisting of 4 consecutive A2V8E1 units, totaling 48 pentapeptide repeats. This stimuli-responsive middle block triggered phase separation of hELPs in response to physiological temperature (37° C.). Finally, the C-terminus of hELPs contained 4 lysine blocks (K-block. GSKGS (SEQ ID NO 011)), which served as the complementary partner to the glutamine residues in the reaction catalysed by FXIIIa.

Full hELP sequence (SEQ ID NO 001):

*MGHGVGVPGVGVPGAGVPGVGVPGVGVPGVGVPGVGVPGVGVPGVGVPGVGVPGEGVPGAGSGDQMMLPWP*

AVALSGVPGVGVPGVGVPGAGVPGVGVPGVGVPGVGVPGVGVPGVGVPGVGVPGVGVPGEGVPGAGSGDQM

*MLPWPAVALSGVPGVGVPGVGVPGAGVPGVGVPGVGVPGVGVPGVGVPGVGVPGVGVPGVGVPGEGVPGAG*

*SGDQMMLPWPAVALSGVPGVGVPGVGVPGAGVPGVGVPGVGVPGVGVPGVGVPGVGVPGVGVPGVGVPGEG*

*VPGAGSGDQMMLPWPAVALSGVPGVGVPGVGVPGAGVPGVGVPGVGVPGVGVPGVGVPGVGVPGVGVPGVG*

*VPGEGVPGAGVPGVGVPGVGVPGAGVPGVGVPGVGVPGVGVPGVGVPGVGVPGVGVPGVGVPGEGVPGAGV*

*PGVGVPGVGVPGAGVPGVGVPGVGVPGVGVPGVGVPGVGVPGVGVPGVGVPGEGVPGAGVPGVGVPGVGVP*

*GAGVPGVGVPGVGVPGVGVPGVGVPGVGVPGVGVPGVGVPGEGVPGAGVPGVGVPGVGVPGAGVPGVGVPG*

*VGVPGVGVPGVGVPGVGVPGVGVPGVGVPGEGVPGAGSGGSKGSSGVPGVGVPGVGVPGAGVPGVGVPGVG*

*VPGVGVPGVGVPGVGVPGVGVPGVGVPGEGVPGAGSGGSKGSSGVPGVGVPGVGVPGAGVPGVGVPGVGVP*

*GVGVPGVGVPGVGVPGVGVPGVGVPGEGVPGAGSGGSKGSSGVPGVGVPGVGVPGAGVPGVGVPGVGVPGV*

*GVPGVGVPGVGVPGVGVPGVGVPGEGVPGAGSGGSKGSSGVPGWLDSLEFIA* conELP sequence (SEQ ID NO 002):

MGHGVGVPGVGVPGAGVPGVGVPGVGVPGVGVPGVGVPGVGVPGVGVPGVGVPGEGVPGAGSGDGMMLPWP

AVALSGVPGVGVPGVGVPGAGVPGVGVPGVGVPGVGVPGVGVPGVGVPGVGVPGVGVPGEGVPGAGSGDGM

MLPWPAVALSGVPGVGVPGVGVPGAGVPGVGVPGVGVPGVGVPGVGVPGVGVPGVGVPGVGVPGEGVPGAG

SGDGMMLPWPAVALSGVPGVGVPGVGVPGAGVPGVGVPGVGVPGVGVPGVGVPGVGVPGVGVPGVGVPGEG

VPGAGSGDGMMLPWPAVALSGVPGVGVPGVGVPGAGVPGVGVPGVGVPGVGVPGVGVPGVGVPGVGVPGVG

-continued

VPGEGVPGAGVPGVGVPGVGVPGAGVPGVGVPGVGVPGVGVPGVGVPGVGVPGVGVPGVGVPGEGVPGAGV

PGVGVPGVGVPGAGVPGVGVPGVGVPGVGVPGVGVPGVGVPGVGVPGVGVPGEGVPGAGVPGVGVPGVGVP

GAGVPGVGVPGVGVPGVGVPGVGVPGVGVPGVGVPGVGVPGEGVPGAGVPGVGVPGVGVPGAGVPGVGVPG

VGVPGVGVPGVGVPGVGVPGVGVPGVGVPGEGVPGAGSGGSGGSSGVPGVGVPGVGVPGAGVPGVGVPGVG

VPGVGVPGVGVPGVGVPGVGVPGVGVPGEGVPGAGSGGSGGSSGVPGVGVPGVGVPGAGVPGVGVPGVGVP

GVGVPGVGVPGVGVPGVGVPGVGVPGEGVPGAGSGGSGGSSGVPGVGVPGVGVPGAGVPGVGVPGVGVPGV

GVPGVGVPGVGVPGVGVPGVGVPGEGVPGAGSGGSGGSSGVPGWLDSLEFIA hELP(4Tg-4Tg) (SEQ ID NO 016)
MGHGVGVPGVGVPGAGVPGVGVPGVGVPGVGVPGVGVPGVGVPGVGVPGVGVPGEGVPGAGSGDQMMLPWP

AVALSGVPGVGVPGVGVPGAGVPGVGVPGVGVPGVGVPGVGVPGVGVPGVGVPGVGVPGEGVPGAGSGDOM

MLPWPAVALSGVPGVGVPGVGVPGAGVPGVGVPGVGVPGVGVPGVGVPGVGVPGVGVPGVGVPGEGVPGAG

SGDQMMLPWPAVALSGVPGVGVPGVGVPGAGVPGVGVPGVGVPGVGVPGVGVPGVGVPGVGVPGVGVPGEG

VPGAGSGDQMMLPWPAVALSGVPGVGVPGVGVPGAGVPGVGVPGVGVPGVGVPGVGVPGVGVPGVGVPGVG

VPGEGVPGAGVPGVGVPGVGVPGAGVPGVGVPGVGVPGVGVPGVGVPGVGVPGVGVPGVGVPGEGVPGAGV

PGVGVPGVGVPGAGVPGVGVPGVGVPGVGVPGVGVPGVGVPGVGVPGVGVPGEGVPGAGVPGVGVPGVGVP

GAGVPGVGVPGVGVPGVGVPGVGVPGVGVPGVGVPGVGVPGEGVPGAGVPGVGVPGVGVPGAGVPGVGVPG

VGVPGVGVPGVGVPGVGVPGVGVPGVGVPGVGVPGEGVPGAGSGDQMMLPWPAVALSGVPGVGVPGVGVPGAGVPG

VGVPGVGVPGVGVPGVGVPGVGVPGVGVPGVGVPGEGVPGAGSGDQMMLPWPAVALSGVPGVGVPGVGVPG

AGVPGVGVPGVGVPGVGVPGVGVPGVGVPGVGVPGVGVPGEGVPGAGSGDQMMLPWPAVALSGVPGVGVPG

VGVPGAGVPGVGVPGVGVPGVGVPGVGVPGVGVPGVGVPGVGVPGEGVPGAGSGDQMMLPWPAVALSGVPG

WLDSLEFIA*

The invention claimed is:

1. A polypeptide consisting of, a. a transglutaminase inhibitor sequence selected from the group consisting of:

i. DQMMLPWPAVAL, (SEQ ID NO 3)

ii. WQHKIDLRYNGA, (SEQ ID NO 4)

iii. SQHPLPWPVLML, (SEQ ID NO 5)

iv. EQFPIAFPRYSI, (SEQ ID NO 6)

v. SEQHLLKWPPWH, (SEQ ID NO 7)

vi. WQIPVDWPPLPP, (SEQ ID NO 8)

vii. DQWMMAWPSLTL, (SEQ ID NO 9) and viii. SQIPMAWPLLSL, (SEQ ID NO 10)

b. a plurality of ELP sequences of the sequence VPGXG (SEQ ID NO 12), wherein each X is independently selected from the group consisting of any proteogenic amino acid except Pro, and c. optionally, a spacer sequence comprising at least one lysine residue wherein the polypeptide consists of an amino acid sequence more than 90% identical to the polypeptide sequence of SEQ ID NO 1 or SEQ ID NO 16, and has at least 85% biological activity of the polypeptide sequence of SEQ ID NO 1 or SEQ ID NO 16.

2. The polypeptide according to claim 1, wherein each X is independently selected from the group consisting of Ala, Val and Glu.

3. The polypeptide according to claim 2, wherein the ratio of Ala:Val:Glu for X is 1-3 Ala:7-10 Val:1 Glu.

4. The polypeptide according to claim 1, wherein the transglutaminase inhibitor sequence consists of DQMMLPWPAVAL (SEQ ID NO 3).

5. The polypeptide according to claim 1, wherein the polypeptide comprises spacer sequence GSKGS (SEQ ID NO 11).

6. The polypeptide according to claim 5, wherein each transglutaminase inhibitor sequence and each spacer sequence are separated by at least 2 ELP sequences, from any other transglutaminase inhibitor and spacer sequence.

7. The polypeptide according to claim 1, comprising 2 to 50 spacer sequences.

8. The polypeptide according to claim 1, wherein the ELP sequences form a contiguous amino acid chain without intervening sequences that are not transglutaminase inhibitor sequences or spacer sequences.

9. The polypeptide according to claim 1, wherein all transglutaminase inhibitor sequences comprised in the polypeptide are comprised within a transglutaminase inhibitor sequence tract, and all spacer sequences are comprised within a spacer sequence tract.

10. The polypeptide according to claim 9, wherein the transglutaminase inhibitor sequence tract and the spacer sequence tract are separated by at least 30 ELP sequences.

11. The polypeptide according to claim 1, comprising 50 to 1200 ELP sequences.

12. The polypeptide according to claim 1, wherein ELP sequences comprise 6 to 15 ELP sequences as a contiguous sequence.

13. A method for treatment of impaired hemostasis, excessive bleeding or coagulopathy, comprising administering the polypeptide according to claim 1 to a subject in need thereof, thereby treating the impaired hemostasis, excessive bleeding or coagulopathy.

14. A nucleic acid sequence encoding the polypeptide according to claim 1.

* * * * *